(12) United States Patent
Abbasian et al.

(10) Patent No.: US 8,746,168 B2
(45) Date of Patent: *Jun. 10, 2014

(54) SYSTEM AND METHOD FOR COATING MEDICAL DEVICES

(75) Inventors: Hamed Abbasian, Mississauga (CA); Pamela Chan, Toronto (CA); Valerio Ditizio, Toronto (CA); Vyacheslav Dudnyk, Mississauga (CA); Zhaopeng Li, Vaughan (CA); Said Loloie, Mississauga (CA); Natali Yakeemovich, Mississsauga (CA); Frank DiCosmo, Richmond Hill (CA)

(73) Assignee: Covalon Technologies, Inc., Mississauga (CA)

( * ) Notice: Subject to any disclaimer, the term of this patent is extended or adjusted under 35 U.S.C. 154(b) by 329 days.

This patent is subject to a terminal disclaimer.

(21) Appl. No.: 12/892,783

(22) Filed: Sep. 28, 2010

(65) Prior Publication Data

US 2011/0100293 A1 May 5, 2011

Related U.S. Application Data

(60) Provisional application No. 61/246,663, filed on Sep. 29, 2009.

(51) Int. Cl.
| | | |
|---|---|---|
| *B05C 3/02* | (2006.01) | |
| *C09D 4/00* | (2006.01) | |
| *A61L 27/34* | (2006.01) | |
| *A61L 29/08* | (2006.01) | |
| *C09D 133/08* | (2006.01) | |
| *C08F 2/48* | (2006.01) | |
| *A61L 31/10* | (2006.01) | |
| *C08J 7/18* | (2006.01) | |
| *C08L 33/08* | (2006.01) | |

(52) U.S. Cl.
CPC ... *C08F 2/48* (2013.01); *C09D 4/00* (2013.01); *A61L 27/34* (2013.01); *A61L 2420/02* (2013.01); *A61L 29/085* (2013.01); *C09D 133/08* (2013.01); *C08L 33/08* (2013.01); *A61L 2400/10* (2013.01); *A61L 31/10* (2013.01); *C08J 7/18* (2013.01)
USPC ........... 118/428; 118/429; 118/423; 118/417; 118/641

(58) Field of Classification Search
USPC .......... 118/429, 423, 428, 417, 641; 396/622, 396/630, 631, 577
See application file for complete search history.

(56) References Cited

U.S. PATENT DOCUMENTS

| 2,458,699 A | 1/1949 | Ginsberg |
| 2,527,959 A | 10/1950 | Quinn |

(Continued)

FOREIGN PATENT DOCUMENTS

| CA | 2234538 A1 | 10/1998 |
| CA | 2516100 | 9/2004 |

(Continued)

*Primary Examiner* — Yewebdar Tadesse
(74) *Attorney, Agent, or Firm* — Tarolli, Sundheim, Covell & Tummino LLP

(57) ABSTRACT

A system and method for photo-grafting a coating polymer onto the surface of a medical device are provided. The system comprises a plurality of stations including a novel grafting station. The system and method of the invention are both time- and resource-efficient. The system includes several stations, each station including a dipping tank. The system allows for the automated, semi-automated, or manual dipping of medical devices into the dipping tanks in a specified order, as desired, wherein at least one of the stations is a grafting station for photo-grafting the coating polymer onto the surface of the medical device. The system is modular, which allows for modification of the process as required, depending on the needs of the user. The system may comprise stations for incorporating an antimicrobial agent into the coating, and/or for rendering the coating lubricious.

93 Claims, 19 Drawing Sheets

(56) References Cited

U.S. PATENT DOCUMENTS

| | | |
|---|---|---|
| 3,502,577 A | 3/1970 | Hutchins et al. |
| 3,511,160 A | 5/1970 | Van Reusel |
| 3,685,997 A | 8/1972 | Kellogg et al. |
| 3,733,993 A | 5/1973 | Lasky |
| 3,739,702 A | 6/1973 | Wender et al. |
| 5,068,681 A * | 11/1991 | Kosugi et al. ............... 396/572 |
| 5,501,669 A | 3/1996 | Conway et al. |
| 6,153,107 A | 11/2000 | Ogawa et al. |
| 6,322,261 B1 | 11/2001 | Kuzyk |
| 6,808,738 B2 | 10/2004 | DiTizio et al. |
| 7,041,174 B2 * | 5/2006 | Carlson et al. ............... 118/695 |
| 2006/0067683 A1 | 3/2006 | Yamashita et al. |

FOREIGN PATENT DOCUMENTS

| | | |
|---|---|---|
| CA | 2695659 A1 | 2/2009 |
| WO | WO-02/070022 A2 | 9/2002 |
| WO | WO-2009/015476 A1 | 2/2009 |

* cited by examiner

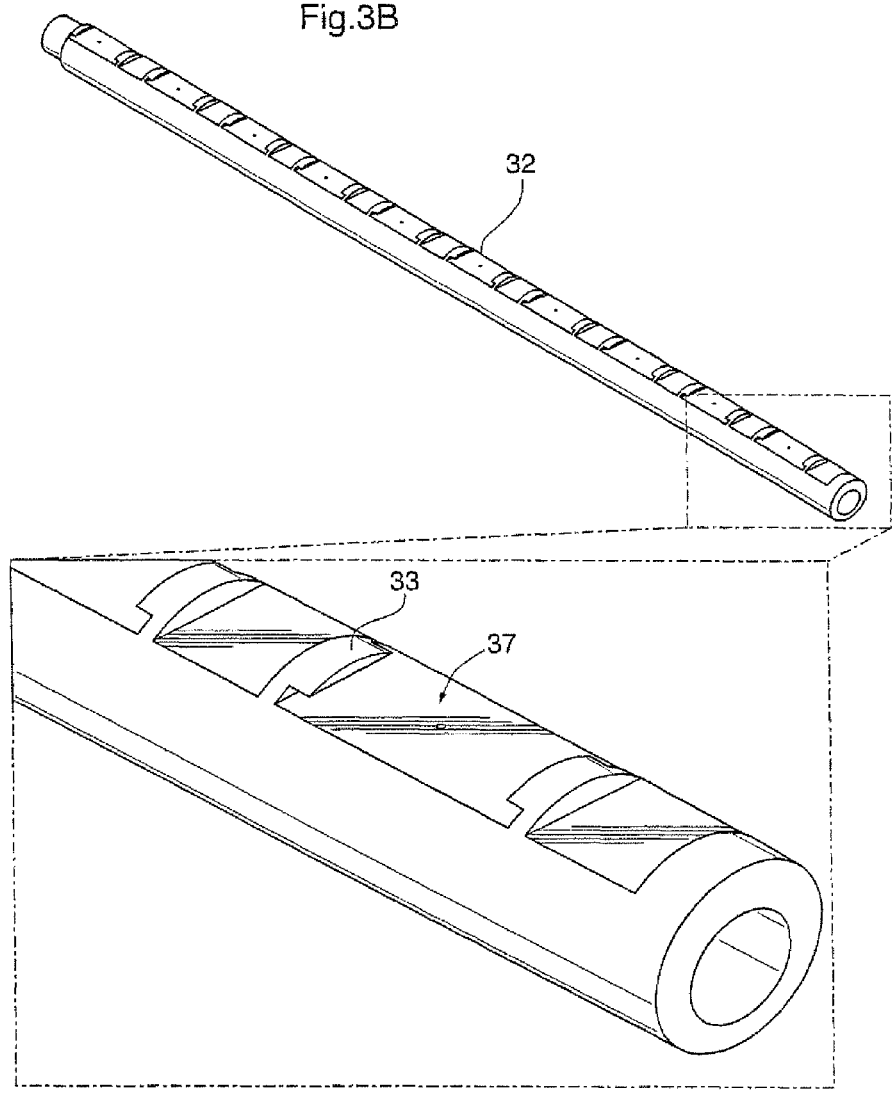

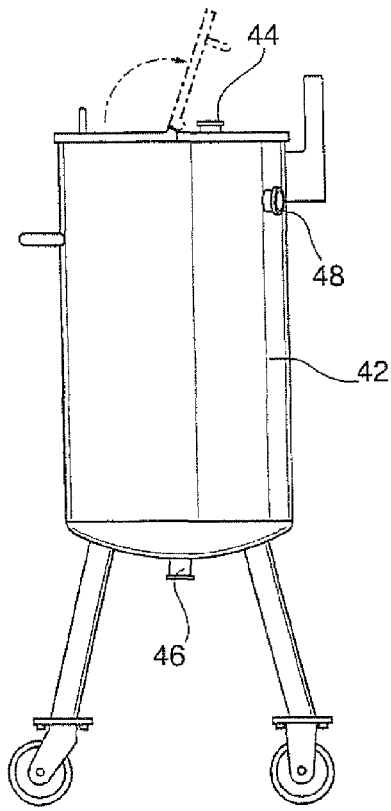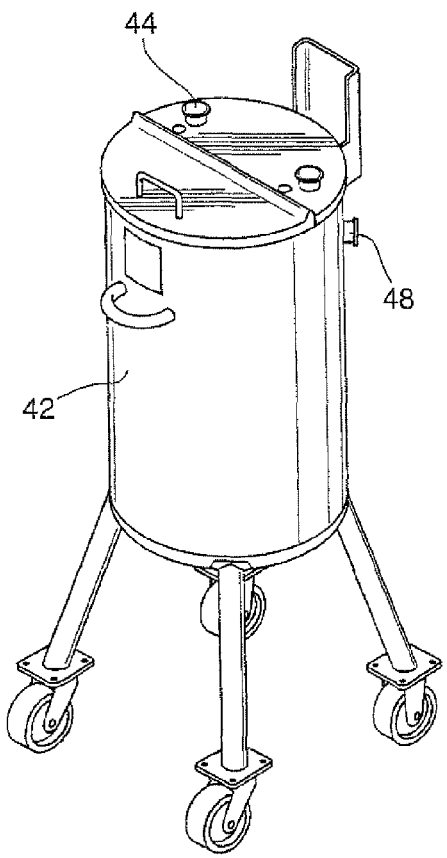
Fig. 6A
Fig. 6B

SYSTEM AND METHOD FOR COATING MEDICAL DEVICES

RELATED APPLICATION

This application claims priority from U.S. Provisional Patent Application Ser. No. 61/246,663, filed on Sep. 29, 2009.

FIELD OF THE INVENTION

This invention relates to a system and method for coating medical devices. More specifically, this invention is directed to a novel system and method for photo-grafting a coating polymer onto the surface of a medical device.

BACKGROUND OF THE INVENTION

Throughout this application, various references are cited to describe more fully the state of the art to which this invention pertains. The disclosures of these references are hereby incorporated by reference into the present disclosure in their entirety.

The use of implanted medical devices is a vital component of current clinical practice, however, complications may arise from their use. Common complications are the physical trauma to the patient's tissues resulting from insertion and continued use of the device, as well as the potential for the device to serve as a focus for microbial contamination and thus, a possible source for microbial infection of the patient. In fact, these complications are often associated since the placement of a medical device, such as a urethral catheter or ureteral stent, may cause tearing and bleeding of delicate tissues thereby creating an opportunity for infection through microbial contamination of the device or through subsequent migration of microbes along the device's surface. It has been therefore desirable to develop better quality in-dwelling biomedical devices made from materials that provide for clinical advantages to a patient.

In response to the problem of insertion-related trauma, polymeric medical devices have been coated with various hydrophilic polymers to produce a more low friction or lubricious coating on the device. The coated devices have high friction surfaces when dry, but upon wetting the devices become slippery and can be more readily inserted into veins, arteries, and other passageways causing minimal tissue damage.

Most of the current grafting methods are resource and time intensive procedures that require multiple manual steps of dipping and waiting, followed by the manual transfer of the devices from one solution to the next. In between each solution submersion step, conventional devices are dried, adding to the time required to complete the grafting method. For example, a grafting method is described in Applicant's WO 02/070022, incorporated herein by reference in its entirety. However, the method comprises intermediate steps of drying and is relatively time and resource intensive since only one device is coated at a time.

There is thus a need to develop an efficient and effective apparatus and system for photo-grafting a coating polymer onto the surface of a medical device, as well as methods and systems incorporating said grafting station, so as to produce clinically useful medical devices having consistent desirable properties of lubricious surfaces and anti-microbial activity, thus obviating at least one problem with that of the prior art.

SUMMARY OF THE INVENTION

The present invention is a novel system and method for photo-grafting a coating polymer onto the surface of a medical device. The system of the invention comprises a plurality of stations including a novel grafting station. The system and method of the invention are both time- and resource-efficient. The system of the invention includes several stations, each station including a dipping tank. The system described herein allows for the automated, semi-automated, or manual dipping of medical devices into the dipping tanks in a specified order, as desired, wherein at least one of the stations is a grafting station for photo-grafting the coating polymer onto the surface of the medical device. The system is modular, which allows for modification of the process as required, depending on the needs of the user. For example, the system may comprise stations for incorporating an antimicrobial agent into the coating, and/or for rendering the coating lubricious.

According to an aspect of the present invention there is provided a grafting station for grafting a coating polymer onto a surface of a wet photoinitiator-coated device, said station comprising:
  i) a grafting tank, for submerging said device into a polymerizable solution;
  ii) a diffuser, disposed within said grafting tank for bubbling an oxygen-scavenging gas from a gas feed into said polymerizable solution; and
  iii) a UV light source, positioned to expose said device to UV light for activating the photoinitiator on said device;
wherein said grafting is effected by submerging said device in said solution while bubbling said gas therethrough and exposing said device to said UV light source.

According to an aspect, the grafting tank comprises a UV light transmissible wall and the UV light source is disposed outside of said grafting tank and adjacent said wall.

According to an aspect, said grafting station comprises a rail for supporting and submerging said device into said polymerizable solution. In an aspect, said rail comprises a mandrel for removably attaching said device to said rail. In an aspect, said rail and mandrel are hollow, defining a contiguous bore ending at an aperture in said mandrel, through which said oxygen-scavenging gas flows from said rail, into said mandrel, and into said polymerizable solution. In another aspect, said rail supports a plurality of devices.

According to another aspect, said submerging is fully automated, semi-automated, or manual, and/or is under the control of a programmable computer.

According to another aspect, said grafting station comprises a plurality of rails arranged in rows to form a pallet. Said pallet may support about 200 devices. Said devices may be supported on said rail such that adjacent devices do not contact one another.

According to another aspect, said grafting tank comprises a reactor sized to receive said rail. Said reactor may comprise an opening flanked by slanted arms, said arms for guiding said rail into said opening. Said reactor may further comprise a plurality of dividers for preventing adjacent devices from contacting one another. According to an aspect, the grafting station comprises a plurality of reactors in tandem, each reactor sized to receive an individual rail.

According to another aspect, said UV light transmissible wall comprises glass, such as quartz or borosilicate glass. The grafting station may comprise two opposing UV light transmissible walls.

In an aspect, said UV light source is a UV light assembly comprising a plurality of UV lights and said UV light assembly comprises a switch for independently powering each of said UV lights. Said switch may be fully automated, semi-automated, or manual. In an aspect, said UV light assembly comprises 13 UV lights of 25 watts each.

In an aspect, said diffuser is disposed inside of said grafting tank near the bottom of said tank or at the bottom of said tank. In another aspect, said gas feed is activated prior to exposing said device to said UV light source and/or is activated simultaneously with exposing said device to said UV light source. Said gas feed may be adjustable and may be fully automated, semi-automated, or manual.

In an aspect, said grafting station further comprises a supply tank for transferring said polymerizable solution to said grafting tank. Said supply tank may comprise a stirrer. Said grafting station in an aspect further comprises a drain tank for transferring said polymerizable solution from said grafting tank and said drain tank may comprise a stirrer.

According to another aspect, said grafting station is fully automated and under the control of a computer system.

According to another aspect, the polymerizable solution is a monomer solution such as acrylic acid, methacrylic acid, 2-carboxyethyl acrylate, 4-vinylbenzoic acid, itaconic acid, methyl acrylate, or combinations thereof. The monomer solution comprises, in an aspect, acrylic acid and methyl acrylate.

According to another aspect, the oxygen-scavenging gas is selected from the group consisting of nitrogen, argon, helium, and combinations thereof and is, in an aspect, nitrogen.

In an aspect, the UV light source has a wavelength of between about 100 nm and about 400 nm, such as between about 300 nm and about 365 nm.

In another aspect, the photoinitiator is selected from the group consisting of peresters, α-hydroxyketones, benzil ketals, benzoins, derivatives thereof, and combinations thereof. The photoinitiator may comprise, for example, 2,2-dimethoxy-2-phenyl-acetophenone (DPA), p-benzoyl tert-butylperbenzoate (BPB), tert-butylperoxybenzoate (TBP), benzophenone (BP) or combinations thereof. In an aspect, the photoinitiator comprises benzophenone and tert-butylperoxybenzoate.

According to another aspect, the device is selected from the group consisting of cardiac valves, dressings, pins, clamps, clips, syringes, syringe accessories, catheters, drains, stents, implants, tubings, ocular lenses, and their delivery devices. In an aspect, the device is a catheter.

According to another aspect of the present invention, there is provided a system for grafting a coating polymer onto a surface of a device, the system comprising:
  a) a photoinitiator station comprising a photoinitiator tank for coating said device with a photoinitiator solution;
  b) a grafting station comprising:
    i) a grafting tank, for submerging said device into a polymerizable solution;
    ii) a diffuser, disposed within said grafting tank for bubbling an oxygen-scavenging gas from a gas feed into said polymerizable solution; and
    iii) a UV light source, positioned to expose said device to UV light for activating the photoinitiator on said device; wherein said grafting is effected by submerging said device in said polymerizable solution while bubbling said gas therethrough and exposing said device to said UV light source; and
  c) a rail, for transferring said device from said photoinitiator tank to said grafting tank without first drying said device.

In an aspect, the grafting tank comprises a UV light transmissible wall and the UV light source is disposed outside of said grafting tank and adjacent said wall.

In an aspect, said rail comprises a mandrel for removably attaching said device to said rail. Said rail and mandrel may be hollow, defining a contiguous bore ending at an aperture in said mandrel, through which said oxygen-scavenging gas flows from said rail, into said mandrel, and into said polymerizable solution. In an aspect, said rail supports a plurality of devices. Said system may comprise a plurality of rails arranged in rows to form a pallet and said pallet may support about 200 devices. In another aspect, said devices are supported on said rail such that adjacent devices do not contact one another.

According to another aspect, said grafting tank comprises a reactor sized to receive said rail. Said reactor may comprise an opening flanked by slanted arms, said arms for guiding said rail into said opening. Said reactor may further comprise a plurality of dividers for preventing adjacent devices from contacting one another. In an aspect, said system comprises a plurality of reactors in tandem, each reactor sized to receive an individual rail.

According to another aspect, said photoinitiator tank comprises a reactor sized to receive said rail. Said reactor may comprise an opening flanked by slanted arms, said arms for guiding said rail into said opening. Said reactor may further comprise a plurality of dividers for preventing adjacent devices from contacting one another. In an aspect, said system comprises a plurality of reactors in tandem, each reactor sized to receive an individual rail.

According to another aspect, said system further comprises an antimicrobial station comprising an antimicrobial tank, said antimicrobial station for coating said device with an antimicrobial solution comprising an antimicrobial agent. In an aspect, said antimicrobial tank comprises a reactor sized to receive said rail. Said reactor may comprise an opening flanked by slanted arms, said arms for guiding said rail into said opening. Said reactor may further comprise a plurality of dividers for preventing adjacent devices from contacting one another. In an aspect, said system comprises a plurality of reactors in tandem, each reactor sized to receive an individual rail.

According to another aspect, said antimicrobial agent is an antibacterial agent, an antifungal agent, or a combination thereof, such as chlorhexidine, triclosan, benzalkonium chloride, ciprofloxacin, gentimicin, a silver agent, or combinations thereof. In an aspect, said silver agent is a silver salt, such as silver phosphate, silver citrate, silver lactate, silver acetate, silver benzoate, silver chloride, silver carbonate, silver iodide, silver iodate, silver nitrate, silver laurate, silver sulfadiazine, silver palmitate, and combinations thereof. In another aspect, said antimicrobial agent is encapsulated and/or associated with a pharmaceutical carrier, such as liposomes, micelles, microcapsules, microspheres, nanospheres, or combinations thereof. According to another aspect, said antimicrobial solution further comprises a stabilizer, such as pyrrolidone carboxylic acid (PCA), Brilliant Green, Crystal Violet, or combinations thereof.

According to another aspect, said system further comprises a surface oxidation station comprising a surface oxidation tank, said surface oxidation station for pre-treating said device with a caustic aqueous solution, such as sodium hydroxide, sulfuric acid, or hydrochloric acid. Said surface oxidation tank may further comprise a temperature control system. In an aspect, said temperature control system maintains the temperature of the caustic aqueous solution within about 10° C. of the desired temperature, such as between about 20° C. and about 90° C. Said surface oxidation tank may further comprise a removable lid.

According to another aspect, said system further comprises a first wash station comprising a first wash tank for rinsing said device. Said system may further comprise a second wash station comprising a second wash tank for rinsing said device. In an aspect, said first wash tank comprises a wash solution selected from the group consisting of water, methanol, ethanol, isopropanol, and combinations thereof. Said wash solution may further comprise up to about 1% of a miscible organic solvent, such as ethyl acetate. In an aspect, said second wash tank comprises purified water.

According to another aspect, said system further comprises a first alkaline station comprising a first alkaline tank for coating said device in a basic solution. Said system may further comprise a second alkaline station comprising a second alkaline tank for coating said device in a basic solution. In an aspect, said first alkaline station further comprises a temperature control system. Said temperature control system in an aspect maintains the temperature of the basic solution within about 10° C. of the desired temperature, such as between about 30° C. and about 70° C. In an aspect, said basic solution is selected from the group consisting of Trizma, sodium hydroxide, ammonia, sodium carbonate, and combinations thereof.

According to another aspect, said system further comprises a drying station comprising a drying chamber. Said drying chamber may comprise a drain valve for draining any residual solution that drips from said device and may further comprise an air filtration and heating system for delivering heated air to said drying chamber. Said heated air is in an aspect at a constant temperature of between about ambient to about 70° C.

According to another aspect, said stations are modular and can be ordered as desired. For example, said stations may be disposed in tandem in a line or may be disposed in a horseshoe arrangement.

According to another aspect, said system further comprises an arm for receiving said rail and raising and lowering said rail into each of said tanks. Said system may comprise one arm per tank.

In another aspect, said system is fully automated and under the control of a computer system.

According to another aspect of the present invention, there is provided a system for rendering a plurality of in-dwelling medical devices lubricious and antimicrobial, the system comprising, in order:
  a) a photoinitiator station comprising a photoinitiator solution;
  b) a grafting station comprising a polymerizable solution, a diffuser, and a UV light source;
  c) a first wash station comprising a basic solution;
  d) a first alkaline station comprising a basic solution;
  e) an antimicrobial station comprising an antimicrobial solution;
  f) a second alkaline station comprising a basic solution;
  g) a second wash station comprising purified water;
said system further comprising a pallet for holding said devices and for transferring said devices from one solution to the next without drying said device.

In another aspect, said system further comprises, before said photoinitiator station, a surface oxidation station for pre-treating said devices.

In another aspect, said system further comprises, after said second wash station, a drying station for drying said devices.

In another aspect, said system further comprises a loading station for loading said devices onto said pallet.

In another aspect, said system further comprises an unloading station for unloading said devices from said pallet.

In another aspect, said stations are arranged in a horseshoe surrounding a central carriage. Said carriage may comprise an arm for receiving said pallet and for raising said pallet into and out of said solutions. Said carriage may comprise a plurality of arms for receiving a plurality of pallets and for raising said pallets into and out of said solutions.

In another aspect, movement of said pallet from one solution to the next is fully automated.

According to another aspect of the present invention, there is provided a method for grafting a coating polymer onto a surface of a device, the method comprising:
  a) submerging said device into a photoinitiator solution;
  b) without first drying said device, submerging said device into a polymerizable solution;
  d) bubbling an oxygen-scavenging gas through said polymerizable solution;
  e) applying a UV light to said device to activate said photoinitiator, thereby grafting said coating polymer onto said surface; and
  f) drying said device.

In an aspect said device is submerged in said photoinitiator solution for from about 20 seconds to about 15 minutes.

In another aspect, said device is submerged in said polymerizable solution for from about 2 minutes to about 20 minutes.

In another aspect, bubbling said gas occurs prior to applying said UV light. In another aspect, bubbling said gas occurs simultaneously with applying said UV light.

In an aspect, said device is dried for about 12 hours.

In another aspect, said method further comprises submerging said device into a surface oxidation solution prior to submerging said device in said photoinitiator solution. Said device may be submerged in said surface oxidation solution for from about 5 minutes to about 60 minutes at a temperature of from about 20° C. to about 90° C.

In another aspect, said method further comprises submerging said device into a first wash solution prior to drying said device. Said device may be submerged in said first wash solution for from about 5 to about 30 minutes.

In another aspect, said method further comprises submerging said device into a first alkaline solution prior to drying said device. Said device may be submerged in said first alkaline solution for from about 10 to about 15 minutes at a temperature at from about 30° C. to about 70° C.

In an aspect, said method further comprises submerging said device into an antimicrobial solution prior to drying said device. Said device may be submerged in said antimicrobial solution for from about 1 minute to about 10 minutes.

In an aspect, said method further comprises submerging said device into a second alkaline solution prior to drying said device. Said device may be submerged in said second alkaline solution for from about 10 to about 15 minutes.

In another aspect, said method further comprises submerging said device into a second wash solution prior to drying said device. Said device may be submerged in said wash solution for from about 5 to about 20 minutes.

According to another aspect, said method comprises:
  a) submerging said device into a surface oxidation solution;
  b) submerging said device into said photoinitiator solution;
  c) without first drying said device, submerging said device into said polymerizable solution;
  d) bubbling said oxygen-scavenging gas through said polymerizable solution;
  e) applying said UV light to said device to activate said photoinitiator, thereby grafting said coating polymer onto said surface;
  f) submerging said device into a first wash solution;
  g) submerging said device into a first alkaline solution;
  h) submerging said device into an antimicrobial solution;
  i) submerging said device into a second alkaline solution;

j) submerging said device into a second wash solution; and
k) drying said device.

In another aspect, said method further comprises packaging said device. Said method may further comprise sterilizing said device.

In another aspect, said device is disposed on a rail for submerging said device into each of said solutions.

In another aspect, said method is fully automated, semi-automated, or manual. In an aspect, said method is under the control of a computer.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

BRIEF DESCRIPTION OF THE DRAWINGS

Embodiments will now be described, by way of example only, with reference to the attached figures, wherein:

FIG. 3B is a perspective view of a mandrel for use with the rail of FIG. 2;

FIG. 6A is a side elevation view of a supply tank for use with the photoinitiator station of FIG. 5;

FIG. 6B is a perspective view of the supply tank of FIG. 6A.

DETAILED DESCRIPTION OF THE INVENTION

Figure 1:
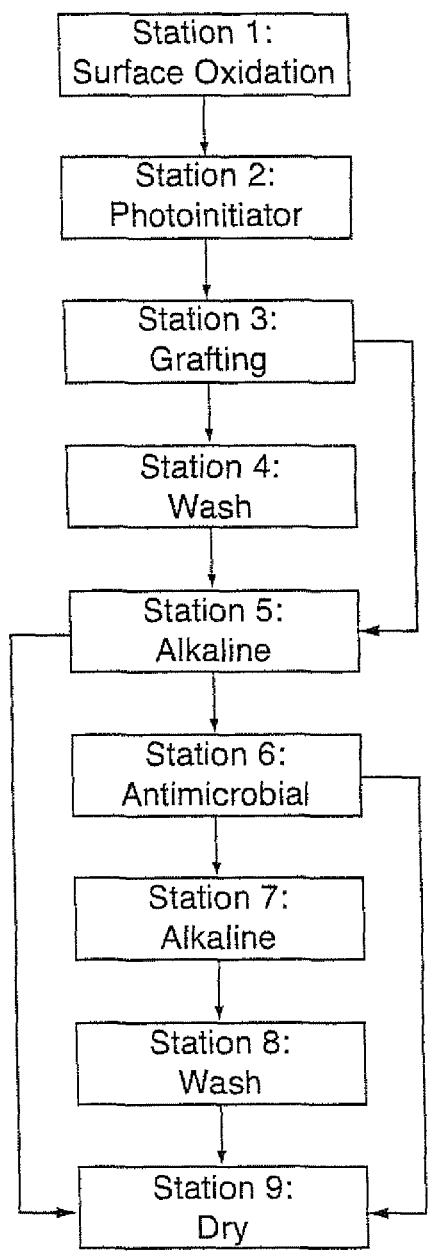
FIG. 1 is a schematic overview of an order of the stations of the system of the invention.

The present invention is a system and method for photo-grafting a coating polymer onto the surface of a medical device. The system of the invention comprises a plurality of stations including a grafting station. The present system and method provide for the large-scale and efficient production of medical devices with lubricious and/or antimicrobial polymeric surfaces that are useful as in-dwelling devices for a variety of different clinical applications. The methods of the invention are mild and efficiently graft the coating polymer onto the surfaces of medical devices in an easy and reliable manner. Furthermore, such surfaces are also provided as lubricious in order to facilitate their clinical in vivo use. The surfaces of the medical devices may also be made to be antibacterial and/or anti-fungal by incorporating an antimicrobial agent therein, in order to treat, ameliorate, prevent, and/or minimize any such infection that may further compromise a patient.

GLOSSARY

A "pallet" is a rack designed to hold medical devices, such as catheters, for coating. In an aspect, the pallet is a light weight, hollow aluminum rack designed to hold about 200 or more catheters. In a further aspect, the catheters or other medical devices are held in the pallet in a plurality of rows formed from rails. A "reactor" is a dipping tank designed for a single row of such medical devices. To process a pallet comprising a plurality of rows of medical devices, stations with reactors require a plurality of reactors, one per pallet rail.

A "tank" or "dipping tank" is a vessel into which the pallet is lowered during processing. In an aspect, the dipping tanks are square or rectangular vessels constructed of stainless steel, such as 316 grade stainless steel, however, it will be understood that the dipping tanks may be made of any suitable shape or material, as would be understood by a skilled person. The dipping tanks may be free draining to a single drain point by gravity. It will be understood that a "reactor" is a specialized type of dipping tank, and reactors and dipping tanks may be used interchangeably in the system and method described below with modifications that would be understood to a skilled person.

A "station" is a single point in the coating process. In an aspect, each station will consist of a dipping tank or set of reactors, a mechanism that facilitates the lowering and raising of the pallet in and out of the dipping tank for processing, and the necessary piping, instrumentation and PLC controls required for that station's purpose in the coating process.

"Sparging" is understood to be a technique which involves bubbling a chemically inert gas, such as nitrogen, argon, or helium, through a liquid. Sparging may be used to remove dissolved gases (e.g. oxygen) from the liquid.

"Lubricious" is understood to mean having a smooth or slippery quality. When medical devices are described as being lubricious, it is understood that the devices, upon wetting, become slippery and can be more readily inserted into veins, arteries, and other passageways causing minimal tissue damage.

The invention is now herein described with reference to the Figures. In the illustrated embodiment, the system is used to coat catheters. FIG. 1 shows an overview of the system of the invention and its component stations. As shown in FIG. 1, there are nine stations: a surface oxidation station; a photoinitiator station; a grafting station; two wash stations; two alkaline stations; an antimicrobial station; and a drying station. The catheters are dipped in the various solutions from station to station, as will be described. It will be evident from the overview schematic shown in FIG. 1 that some stations are optional and may not be required in all coating processes.

However, it will be understood that the novel grafting station is included in each of the various embodiments of the system of the invention.

Figure 2:
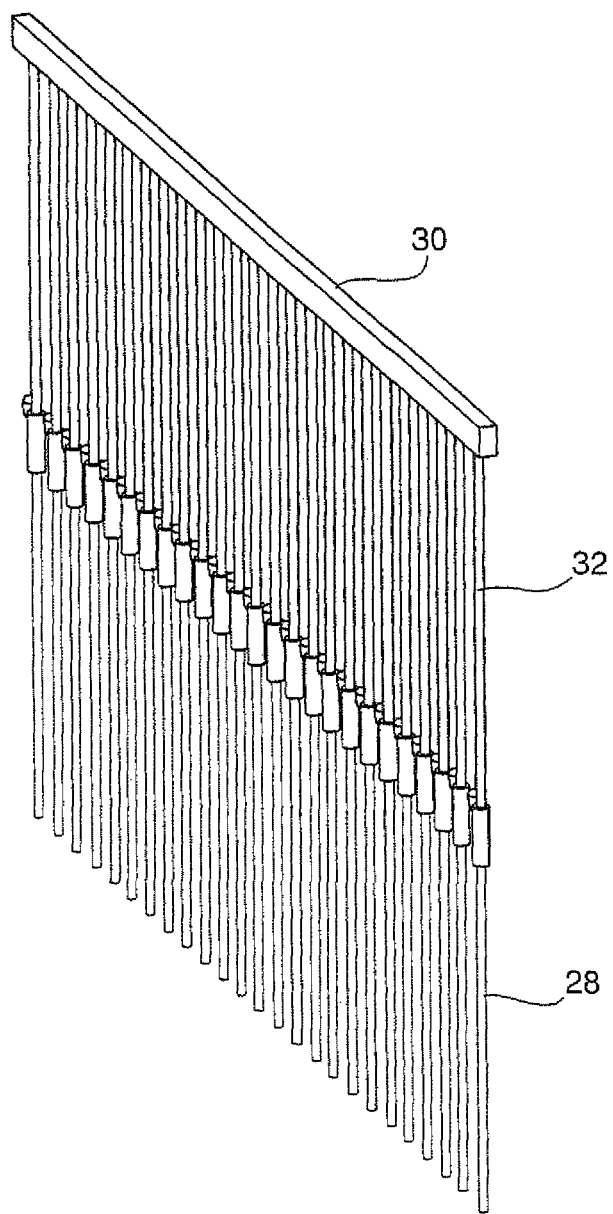
FIG. 2 is a perspective view of a rail for holding catheters for use in the system of FIG. 1.

Referring now to FIG. 2, a rail 30 is shown, on which each catheter 28 is disposed. The rail 30 is for dipping a number of catheters 28 in the tanks at each station. In an aspect, each rail 30 consists of a hollow aluminum extrusion with a row of anodized hollow aluminum mandrels 32 drilled into the extrusion. Each mandrel 32 is inserted into the end of a catheter 28, and holds the catheter 28 in place throughout the coating process. The catheters 28 are attached to the mandrels 32 such that solution can flow into the interior cavities of the catheters 28. The catheters 28 are disposed on the mandrels 32 at a density such that adjacent catheters 28 do not contact one another.

Figure 3A:
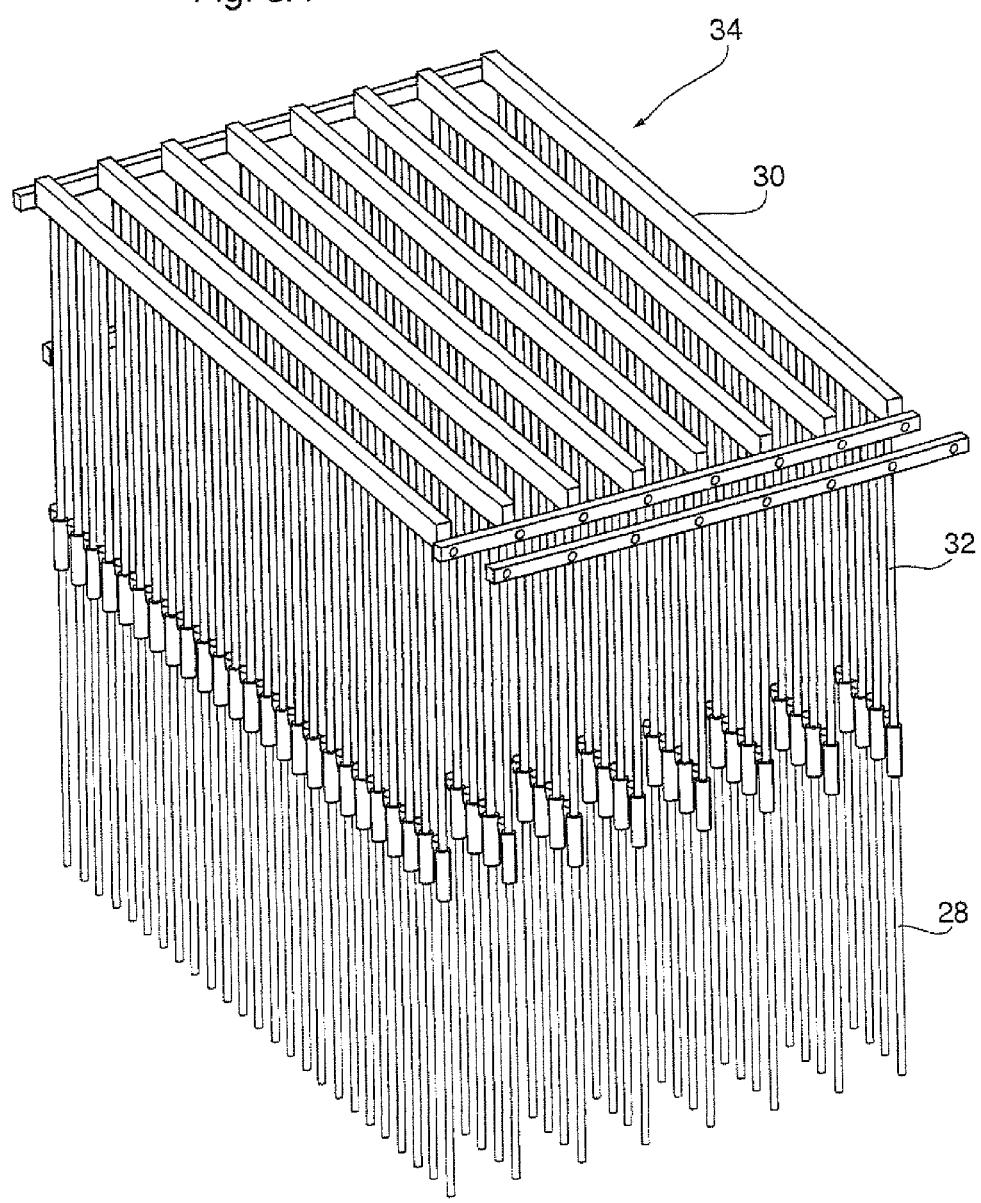
FIG. 3A is a perspective view of a plurality of the rails of FIG. 2, formed into a pallet.

A series of rails 30 is assembled in rows within a frame to create a pallet 34, as is shown in FIG. 3A. The hollow rails 30 and hollow mandrels 32 are used to distribute nitrogen in some parts of the coating process. Nitrogen flows through the hollow rails 30 into the hollow mandrels 32. Each mandrel 32 has an aperture at the bottom end, allowing nitrogen to flow from the mandrel 32 into the catheter 28 attached thereto. The nitrogen then flows out of the bottom of the catheter 28 and, when the catheter 28 is submersed in the solution, the nitrogen then flows into the solution itself. The pallet 34 is transferred from station to station with the catheters 28 attached thereto.

Figure 3C:
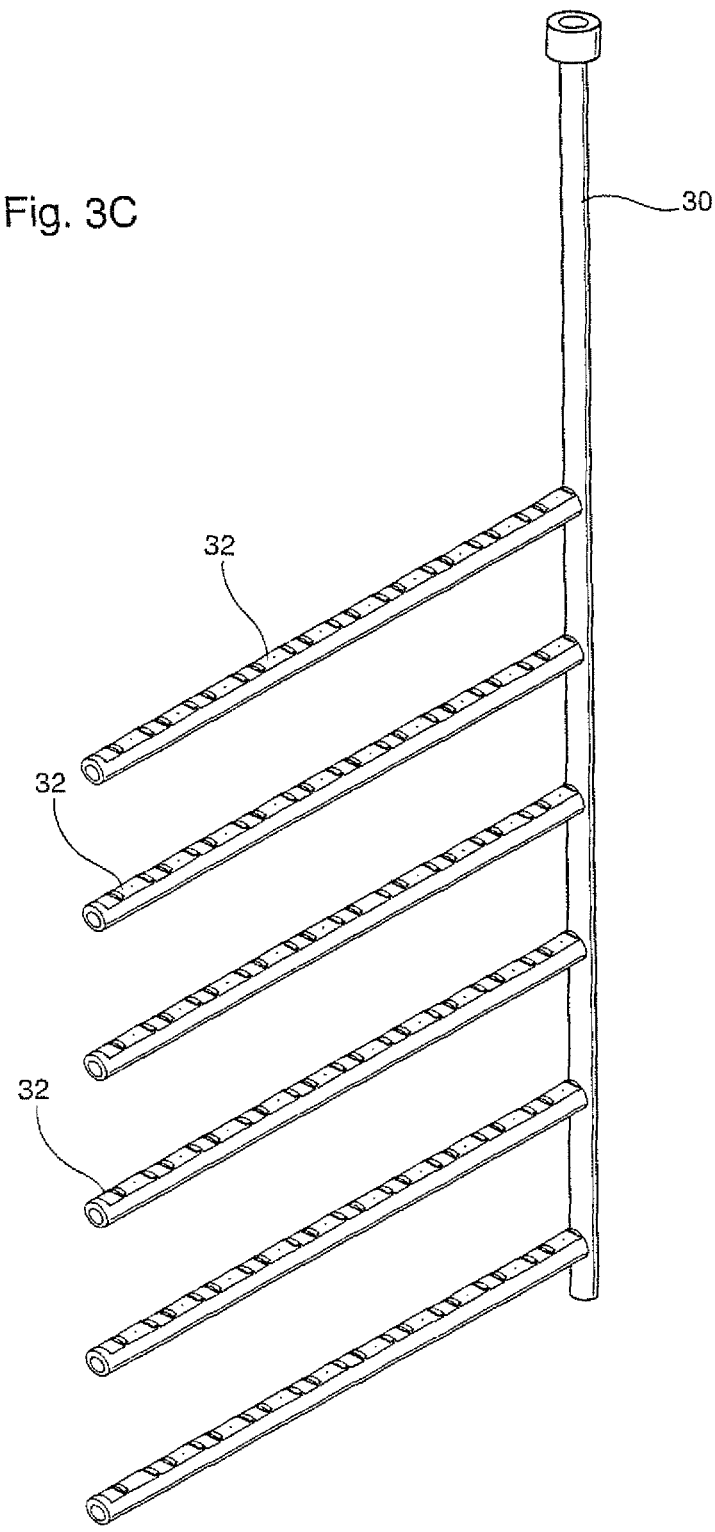
FIG. 3C is a perspective view of the mandrel of FIG. 3B mounted on a rail.

It will be understood that the mandrels 32 could be modified to hold any type of device in place and are not limited to holding catheters 28. In one non-limiting example, referring now to FIGS. 3B and 3C, the device to be coated comprises a flange at one end. An example of such a device is an intraocular lens delivery device. To hold the device in place on the mandrels 32, the mandrels 32 may be provided with engaging members 33 that receive and hold the device in place. In an aspect, the engaging members 33 are brackets. In this aspect, the mandrels are provided with a plurality of apertures 37 along their length so as to allow nitrogen to flow from the mandrel 32 into the interior of each device. A plurality of mandrels 32 comprising the engaging members 33 are shown attached to a rail 30 in FIG. 3C.

Surface Oxidation Station

Figure 4:
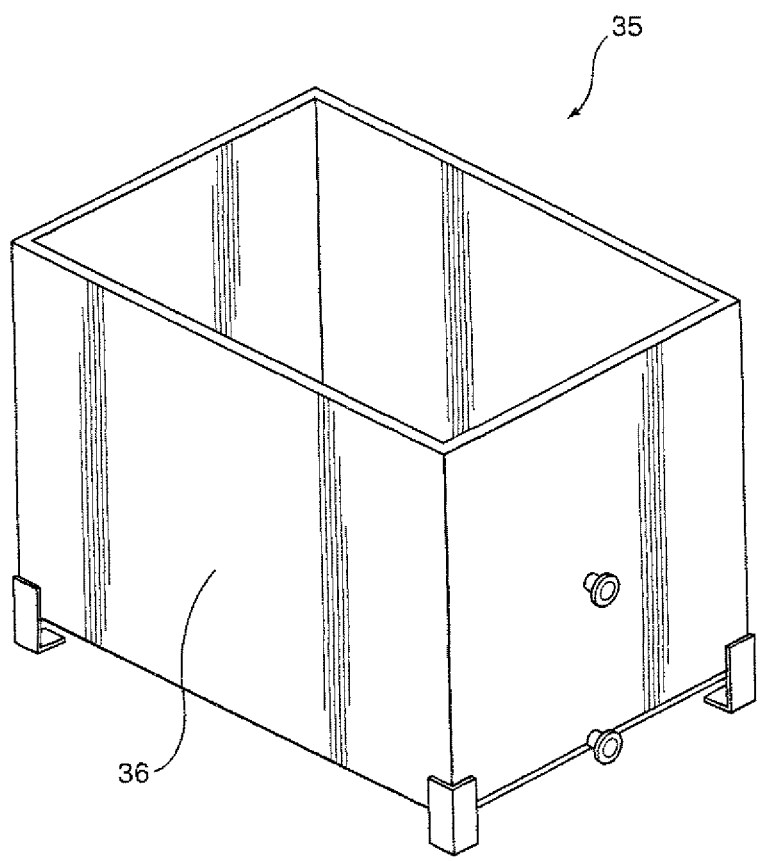
FIG. 4 is a perspective view of the surface oxidation station of the system of FIG. 1.

The first station in the grafting system is a pre-treatment surface oxidation station 35 intended to activate the surface of the catheters 28 for subsequent polymer grafting via free radical chemistry. The surface oxidation station 35 is an optional station intended to be used for when coating extremely inert catheters 28 or other medical devices that are not likely to be able to participate in free radical reactions without oxidation of existing polymer bonds. Examples of materials that would benefit from initial surface oxidation include polytetrafluorethylene, polyetheretherketones, and polyoxymethylene. The surface oxidation station 35 comprises a dipping tank 36, as is shown in FIG. 4. The dipping tank 36 is sized to hold all 200 catheters 28 contained on the pallet 34. The dipping tank 36 may be filled manually with a caustic aqueous solution of base or acid, such as, for example, sodium hydroxide, sulfuric acid, or hydrochloric acid. The surface oxidation station 35 comprises a temperature control system for heating the dipping tank 36 contents and maintaining the temperature within about 10° C. of that which is desired. In an aspect, the desired range of temperatures is between about 20° C. and about 90° C. The dipping tank 36 also comprises a removable lid for containing the solution vapors when the dipping tank 36 is not in use. The catheters 28 remain in the caustic solution for from about 5 to about 60 minutes.

Photoinitiator Station

Figure 5A:
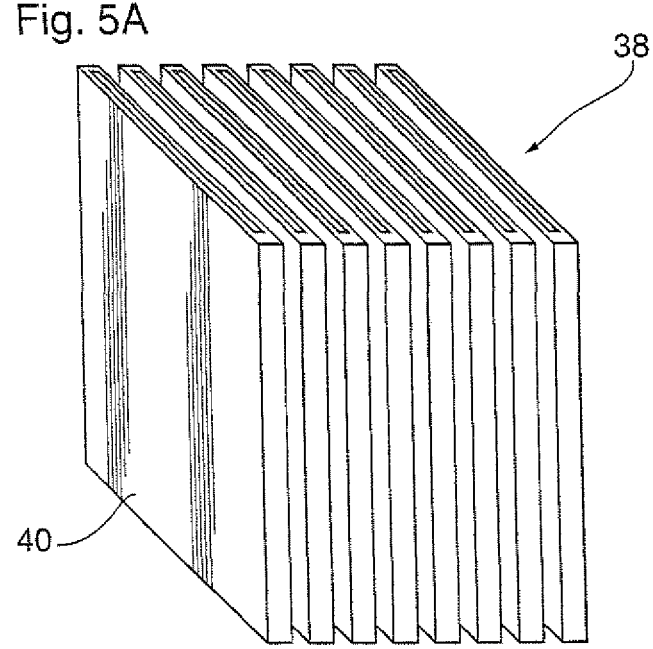
FIG. 5A is a perspective view of the photoinitiator station of the system of FIG. 1 showing a plurality of reactors.
Figure 5B:
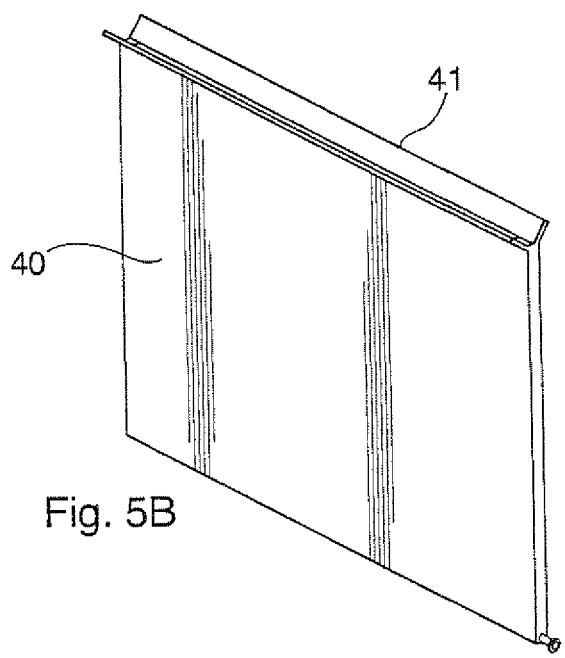
FIG. 5B is a perspective view of an alternate embodiment of a reactor of the station shown in FIG. 5A.

The second station in the grafting system is a photoinitiator station 38, as is shown in FIG. 5A. The photoinitiator station 38 comprises a dipping tank into which the catheters may be dipped. In the illustrated embodiment, the dipping tank is divided into several photoinitiator reactors 40 collectively capable of holding 200 catheters. In an aspect, each of the photoinitiator reactors 40 comprises slanted arms 41 for aiding in guiding the catheters into the reactor cavity, as is shown in FIG. 5B. The photoinitiator reactors 40 hold a photoinitiator solution and it will be understood that the tank is split into several reactors 40 so as to conserve the solution and reduce waste. However, the photoinitiator station 38 could instead simply comprise a single dipping tank large enough in which to dip all 200 catheters on the pallet 34. The photoinitiator reactors 40 comprise a level sensor to detect the level of solution therein. In an aspect, the photoinitiator solution is a mixture of benzophenone and tert-butylperoxybenzoate. The catheters remain in the photoinitiator solution for from about 20 seconds to about 15 minutes. The photoinitiator reactors 40 are interconnected so as to allow simultaneous filling, which is facilitated by the level sensor, which is located outside of the tank. The photoinitiator reactors 40 may be filled manually or by using a supply tank 42, as is shown in FIGS. 6A and 6B.

The supply tank 42 is equipped with a solution entry port 44 at the top and an exit port 46 at the bottom. The size of the supply tank 42 is determined based upon the volume required to fill the photoinitiator reactors 40 during operation, allowing for liquid holdup in supply piping and a safety factor. The supply tank 42 delivers photoinitiator solution to the photoinitiator reactors 40 via the exit port 46 using a centrifugal pump. The centrifugal pump may also function to drain the photoinitiator reactors 40 as needed, returning the photoinitiator solution to the supply tank 42 via a sidewall inlet port 48, using valving to divert the solution flow to the correct flowpath. Similarly to the photoinitiator reactors 40, the supply tank 42 also comprises a level sensor to determine the volume of solution present therein. Between filling and draining operations, the supply tank 42 recirculates the photoinitiator solution from the exit port 46 to the sidewall inlet port 48, thereby mixing the solution.

Grafting Station

Figure 7:
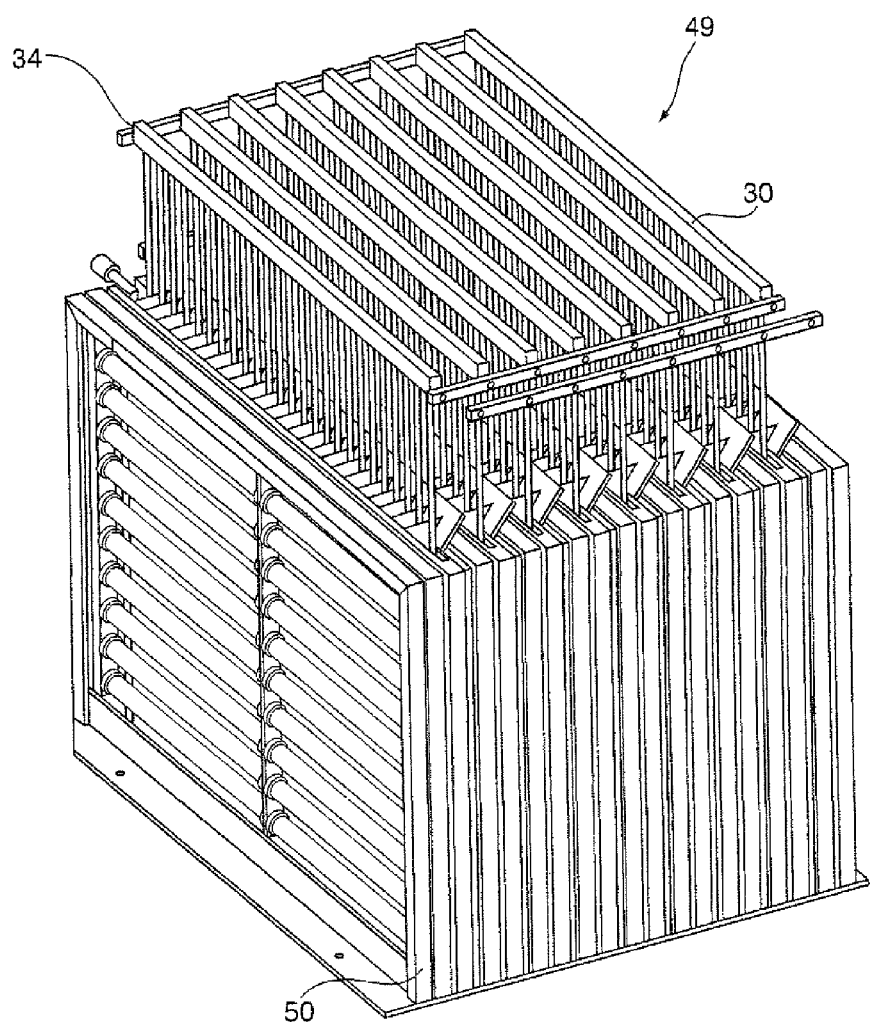
FIG. 7 is a perspective view of the grafting station of the system of FIG. 1 showing a plurality of grafting reactors.
Figure 8:
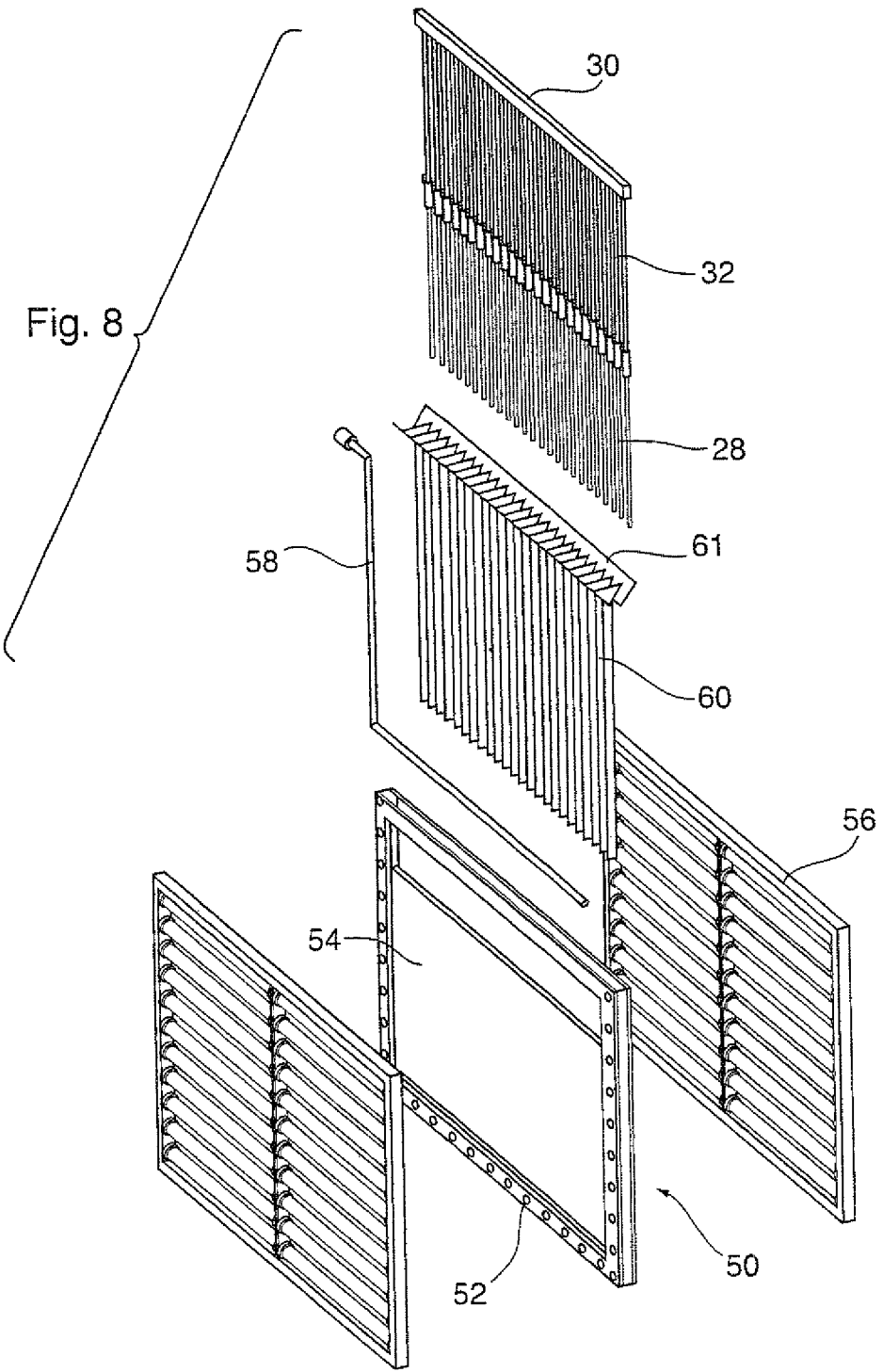
FIG. 8 is perspective view of the components of a grafting reactor of the grafting station of FIG. 7.

The third station in the grafting system is the grafting station 49, as is shown in FIG. 7. The grafting station 49 comprises a dipping tank into which the catheters may be dipped. In the illustrated embodiment, the dipping tank is divided into several grafting reactors 50 collectively capable of holding 200 catheters. The grafting reactors 50 hold a polymerizable solution, which forms a coating polymer when grafted onto the surface of a device. In an aspect, the polymerizable solution is a monomer solution, such as a mixture of acrylic acid and methyl acrylate. Referring now to FIG. 8, a single grafting reactor 50 is shown. Each grafting reactor 50 is formed from an anodized aluminum frame 52 and comprises UV light transmissible walls 54 made of glass. In an aspect, the walls 54 are made of quartz or borosilicate glass, however, it will be understood that the walls 54 can be made from any material that can transmit UV light with a wavelength greater than about 300 nm. Each grafting reactor 50 is flanked by UV light assemblies 56, which shine UV light through the walls 54 and into the interior of the grafting reactors 50. In this way, the catheters 28 may be dipped into the polymerizable solution and exposed to UV light simultaneously. The UV light assemblies 56 comprise a switch for adjusting the number of lights that are turned on, depending upon the size and number of medical devices being coated.

For example, the UV light assemblies 56 may be operated in a "catheter mode", whereby only those lights required for the dipping height of the catheters will be turned on. In an aspect, each UV light assembly comprises 13 lights of 25 watts each.

Nitrogen gas is fed into a diffuser 58, disposed at the bottom interior of the grafting reactor 50, for delivering nitrogen gas to the polymerizable solution and thereby sparging the polymerizable solution of oxygen. In an aspect, sparging is performed while the catheters 28 are in place inside of the grafting reactor 50 but before the catheters 28 are exposed to UV light. In another aspect, sparging is further performed during UV light exposure. Nitrogen gas is also fed into the rails 30 of the pallet 34 using nitrogen supply lines with connection ports to the pallet 34. A nitrogen tank with a pressure regulator and gauge feeds nitrogen to the grafting reactor 50. The nitrogen feeds are adjustable so as to provide a suitable level of gas diffusion within the grafting reactor 50, as will be understood by a skilled person. A divider 60, made of anodized aluminum, is inserted into each grafting reactor 50 to prevent catheters from touching one another during the grafting process. As discussed above with respect to the photoinitiator reactors 40, the dividers 60 may comprise slanted arms 61 for guiding the catheters therein. The catheters remain in the polymerizable solution for from about 2 to about 20 minutes.

A supply tank 62 and a drain tank 63 (shown in FIGS. 15 to 17) are included in the grafting station 49. These tanks 62, 63 are similar to the tank shown in FIGS. 6A and 6B and are used to transfer the polymerizable solution to and from the grafting reactors 50. In an aspect, one or both of the supply 62 and drain tanks 63 of the grafting station are equipped with a stirrer near the bottom.

First Wash Station

Figure 9:
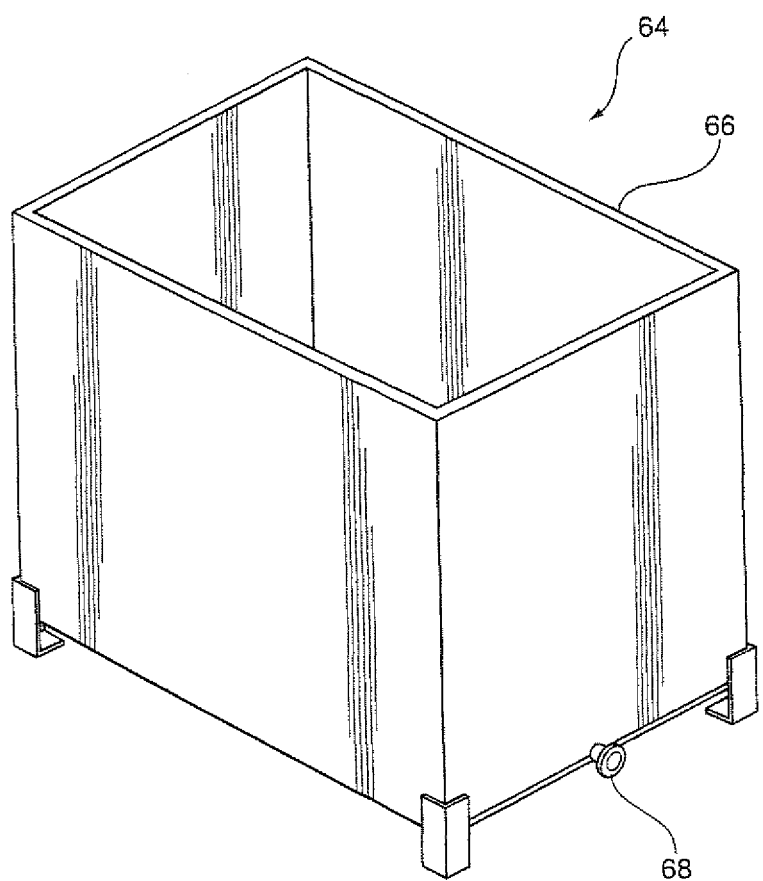
FIG. 9 is a perspective view of the first wash station of the system of FIG. 1.

The fourth station in the grafting system is a first wash station 64 for dipping the catheters 28 in a wash solution. The wash solution comprises, for example, water, methanol, ethanol, isopropanol or mixtures thereof. Additionally, the wash station may contain traces (up to about 1%) of other miscible organic solvents, such as ethyl acetate. Dipping the catheters 28 in the wash solution removes residual photoinitiator or polymerizable solution from the catheters. The first wash station comprises a wash dipping tank 66, as is shown in FIG. 9. The wash dipping tank 66 is capable of holding 200 catheters. The wash dipping tank 66 may be filled manually and comprises an outlet port 68 at the bottom for draining the ethanol. The wash dipping tank 66 comprises a removable lid for containing the ethanol vapors when the wash dipping tank 66 is not in use. The catheters remain in the wash solution for from about 5 to about 30 minutes.

First Alkaline Station

Figure 10:
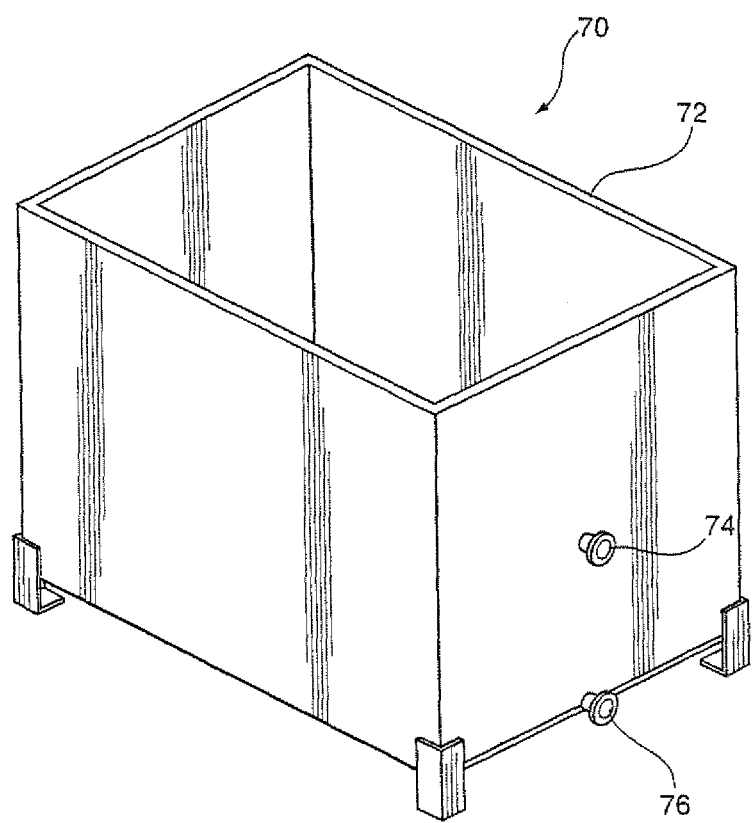
FIG. 10 is a perspective view of the first alkaline station of the system of FIG. 1.

The fifth station in the grafting system is a first alkaline station 70 for dipping the catheters in a basic solution, such as a Trizma solution, or a solution containing one or more bases such as sodium hydroxide, ammonia, or sodium carbonate. The first alkaline station comprises an alkaline dipping tank 72, as is shown in FIG. 10. The alkaline dipping tank 72 is capable of holding 200 catheters 28. The alkaline dipping tank 72 comprises an inlet port 74, an outlet port 76, and a recirculation pump that is housed beneath the alkaline dipping tank 72 for gently and constantly recirculating the alkaline solution through the alkaline dipping tank 72 and the catheters 28. The first alkaline station 70 comprises a temperature control system, also housed beneath the tank, for heating the alkaline dipping tank 72 contents and maintaining the temperature within about 10° C. of that which is desired. In an aspect, the desired range of temperatures is between about 30° C. and about 70° C. The alkaline dipping tank 72 also comprises an inlet with a calibrated flow meter for introducing purified water. The first alkaline station 70 activates the surface of the catheters 28 so as to receive the silver ions in the sixth station in the grafting system.

Antimicrobial Station

Figure 11:
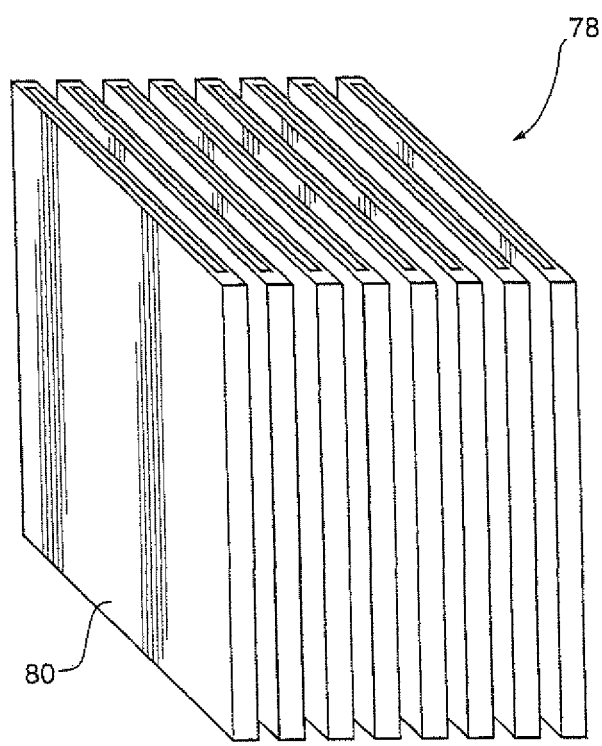
FIG. 11 is a perspective view of the antimicrobial station of the system of FIG. 1.

The sixth station in the grafting system is an antimicrobial station 78, for dipping the catheters into an antimicrobial solution, such as a silver solution. It will be understood that any hydrophilic antimicrobial agent and mixtures of such antimicrobial agents may be applied to the catheters 28 at this stage. Non-limiting examples include chlorhexidine, triclosan, benzalkonium chloride, ciprofloxacin, and gentimicin. Typically, the antimicrobial solution is acidic, due to the nature of the antimicrobial agent(s) therein. The antimicrobial station 78 comprises a dipping tank or a series of interconnected antimicrobial reactors 80, as is shown in FIG. 11. The antimicrobial reactors 80 are similar to the photoinitiator reactors 40 described above and may comprise slanted arms for guiding the catheters into the reactors. It will also be understood that the antimicrobial station 78 could instead consist of a single dipping tank large enough in which to dip all 200 catheters on the pallet 34, as described above for the photoinitiator station 38. The catheters remain in the antimicrobial solution for from about 1 to about 10 minutes. The antimicrobial station 78 also comprises a supply tank 81 (shown in FIGS. 15 to 17), which is identical to the supply tank 42 described above in reference to the photoinitiator station 38. In addition to the antimicrobial agent, the antimicrobial solution may comprise ancillary components to promote coating stability, such as PCA and Crystal Violet, which act to protect silver from the destabilizing influence of light.

Second Alkaline Station

Figure 12:
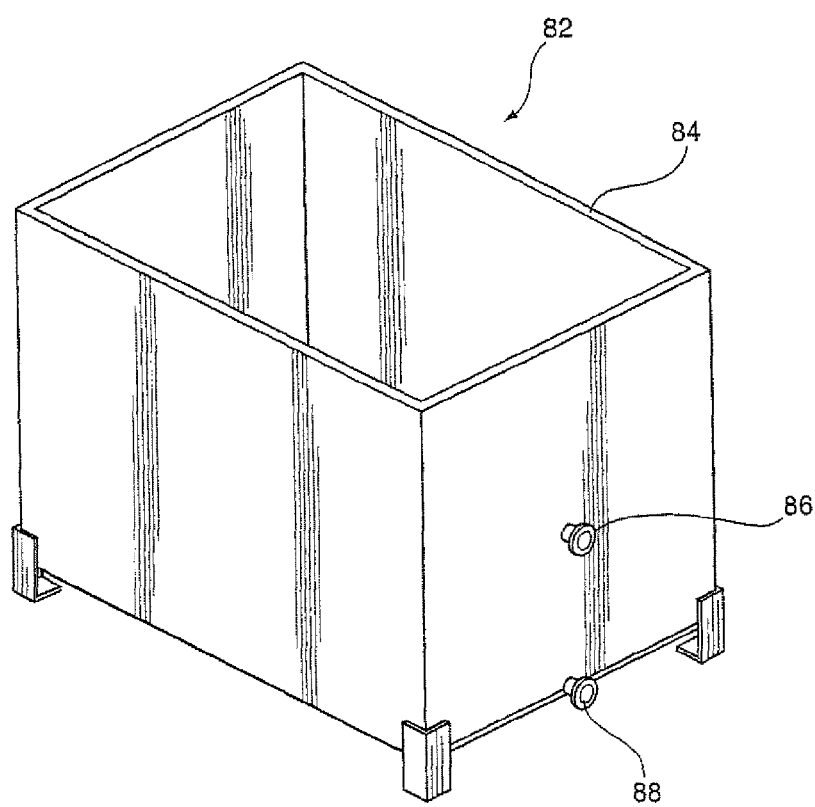
FIG. 12 is a perspective view of the second alkaline station of the system of FIG. 1.

The seventh station in the grafting system is a second alkaline station 82, as is shown in FIG. 12. It will be evident that the second alkaline station 82 is similar to the first alkaline station 70 described above and consists of an alkaline dipping tank 84 comprising an inlet port 86, an outlet port 88, and a recirculation pump for gently and constantly recirculating the alkaline solution through the second alkaline tank 82 and the catheters 28 therein. This step compensates for the acidity of the antimicrobial solution and regenerates the lubricious nature of the coating that may have been partially lost due to dipping in the antimicrobial solution. The alkaline dipping tank 84 does not require a temperature control system as the second alkaline solution does not require heating. The catheters remain in the second alkaline solution for from about 10 to about 15 minutes.

Second Wash Station

Figure 13:
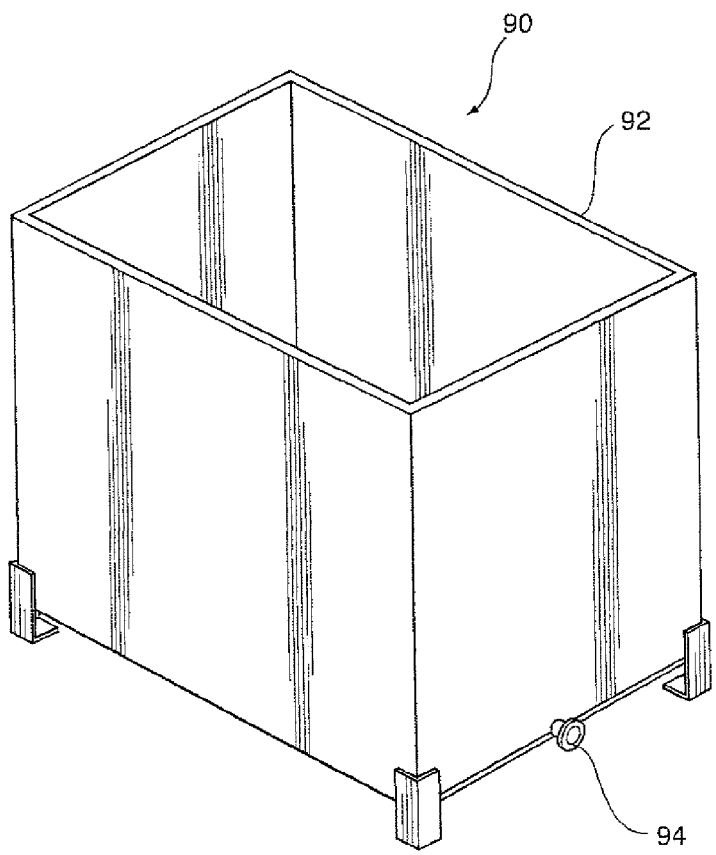
FIG. 13 is a perspective view of the second wash station of the system of FIG. 1.

The eighth station in the grafting system is a second wash station 90 for rinsing the catheters 28 in purified water, as is shown in FIG. 13. The second wash station 90 comprises a wash tank 92 into which purified water is introduced from an inlet port 94. Water flow is controlled by a water supply control system that comprises a calibrated flow meter. The catheters 28 remain in the water rinse for from about 5 to about 20 minutes.

Drying Station

Figure 14:
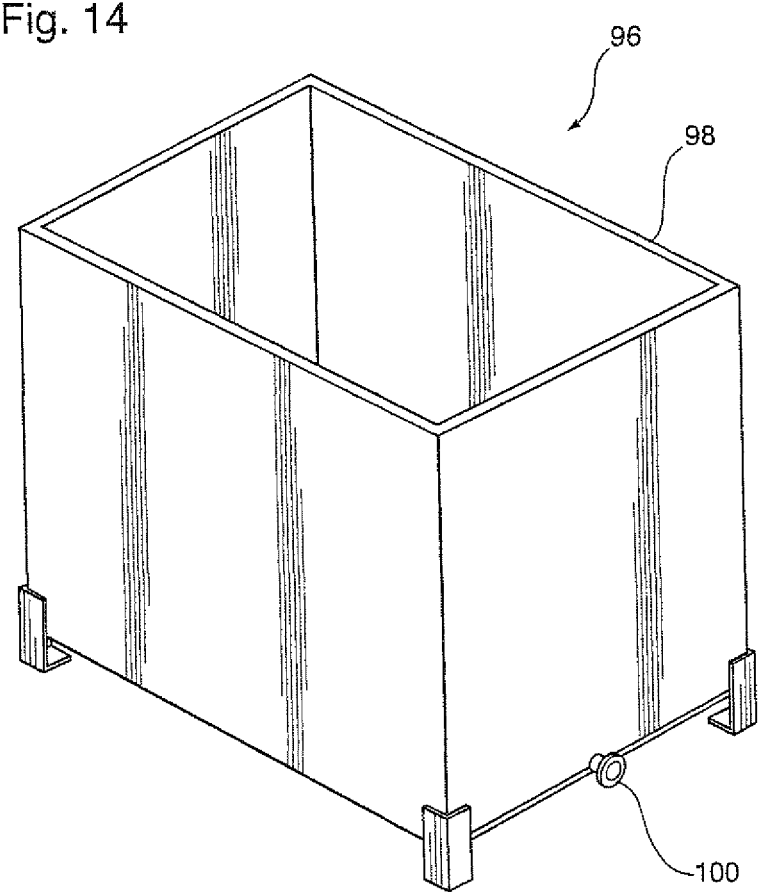
FIG. 14 is a perspective view of the drying station of the system of FIG. 1.

The ninth station in the grafting system is a drying station 96, as is shown in FIG. 14. The drying station comprises a drying chamber 98 capable of holding 200 catheters. A drain valve 100 is located at the bottom of the drying chamber 98 to drain any solution that drips from the catheters during the drying process. An air filtration and heating system, located below and beside the tank, delivers air to the drying chamber 98 at a constant temperature from between about ambient to about 70° C. The air flow provided to the drying chamber 98 is low flow and low pressure so as to create gentle air flow through the drying chamber 98. The catheters are dried in the drying chamber for from about 10 to about 30 minutes and are then transferred to drying racks for at least about 12 hours of drying time at ambient temperatures and conditions.

It will be understood that each specific product will have its own specific set of ideal dwell times in each solution and the above-described times are considered non-limiting. The processes of the invention are considered to be "wet processes" as the products are not dried between each step. This permits a faster operation and coating process as compared to processes that require drying in between various steps.

Grafting System

Figure 15:
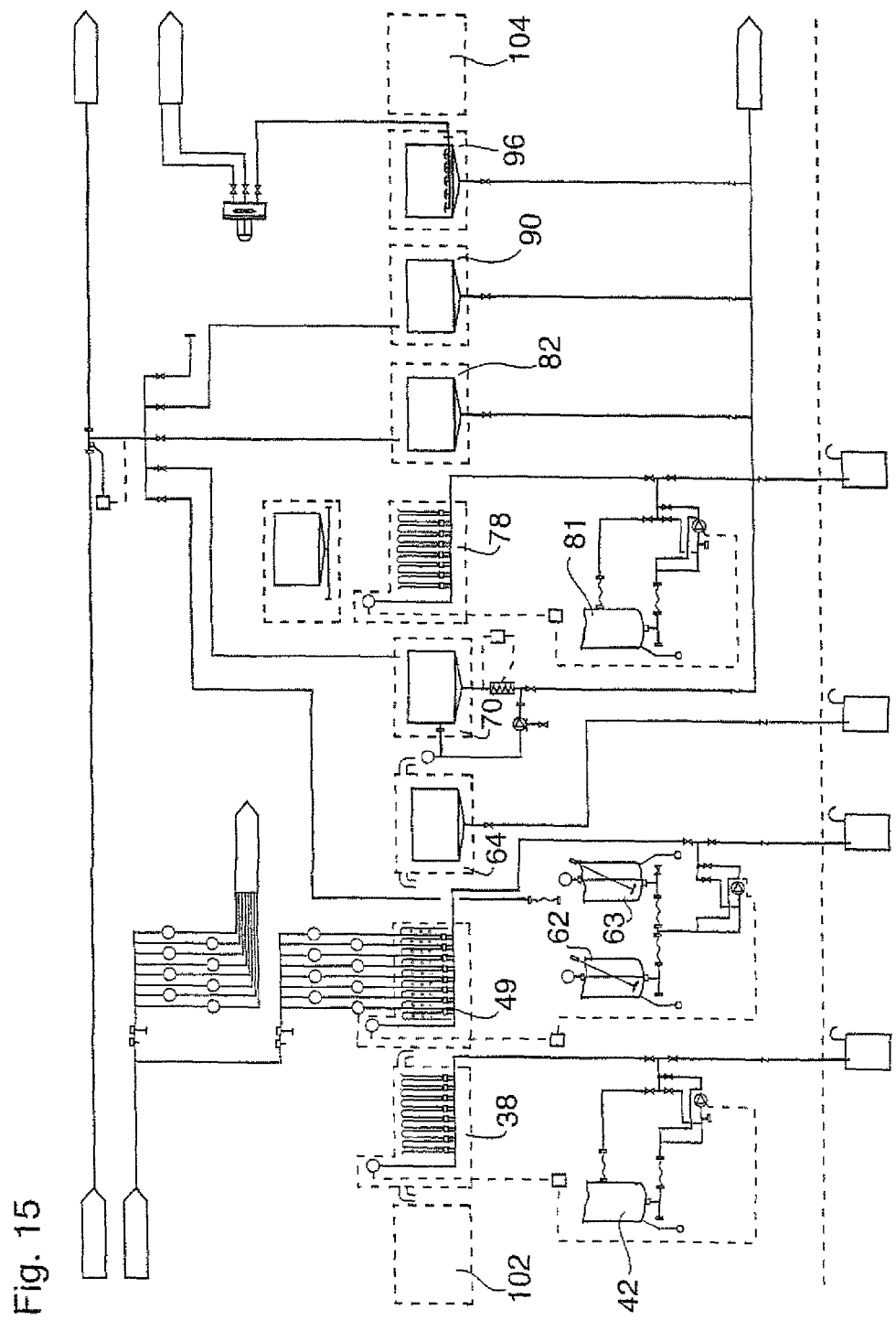
FIG. 15 is a schematic of the system of FIG. 1, showing the stations and auxiliary equipment.
Figure 16:
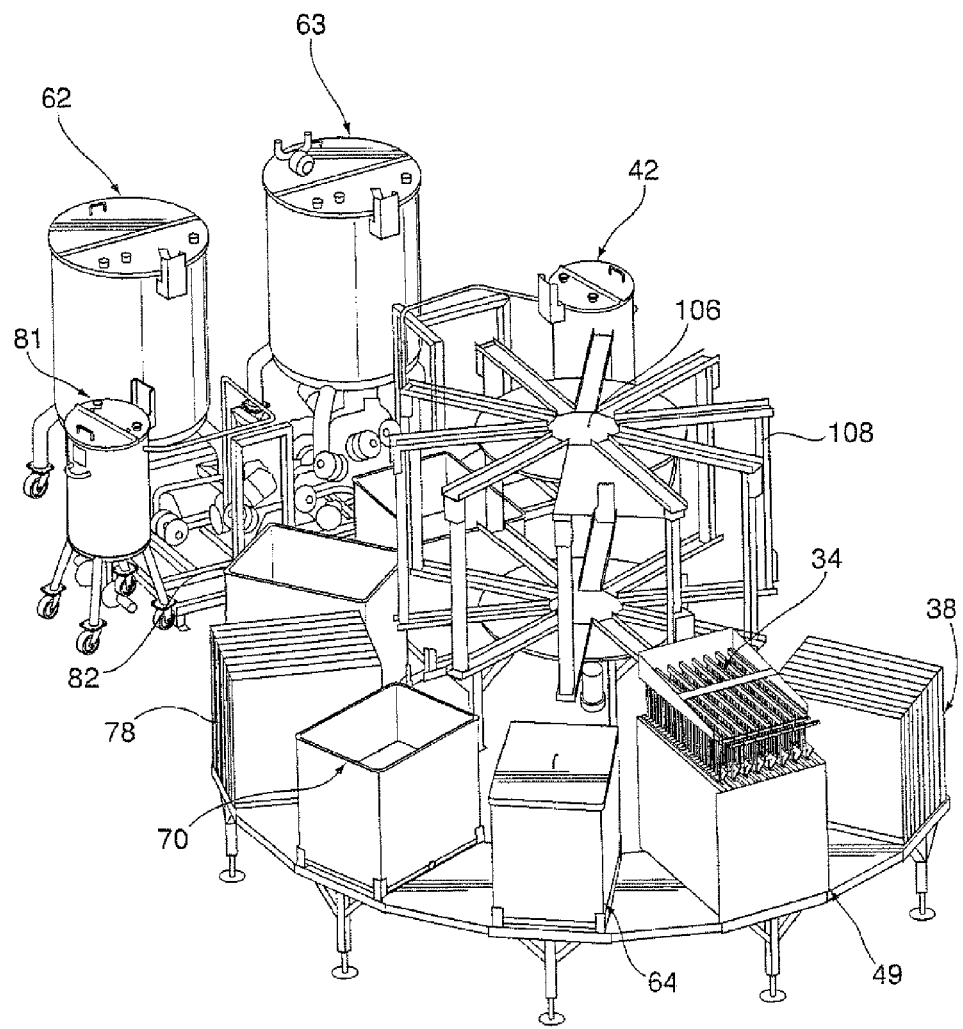
FIG. 16 is a perspective view of the system of FIG. 1, showing the stations and auxiliary equipment.
Figure 17:
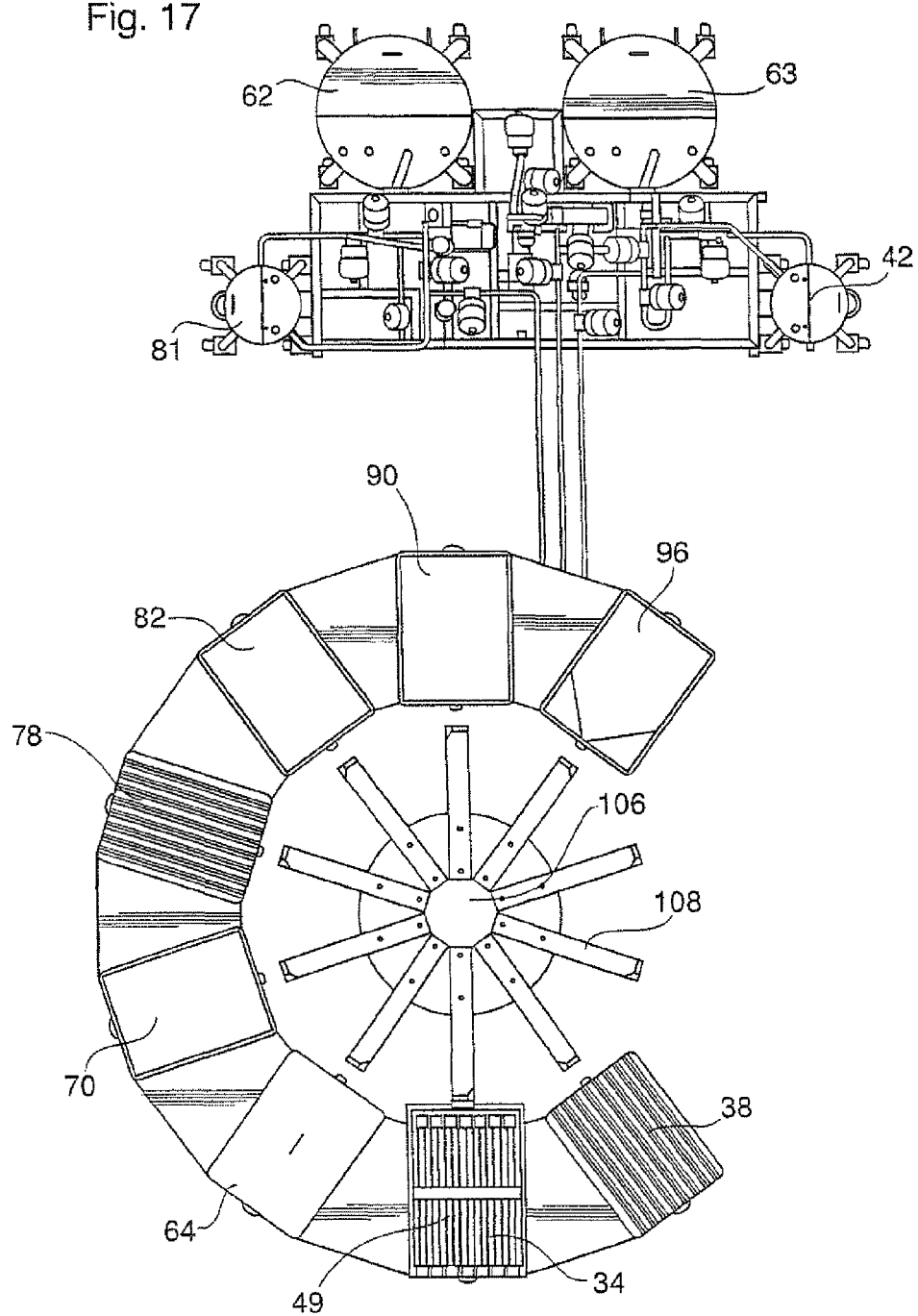
FIG. 17 is a top plan view of the system of FIG. 1, showing the stations and auxiliary equipment.

An aspect of the grafting system of the invention, comprising eight of the stations described above and auxiliary equipment, is shown in FIGS. 15 to 17. The system may additionally comprise a loading station 102 and an unloading station 104 for attaching the catheters to the pallets 34. The stations may be set up in a row, as is shown in FIG. 15, or in a circle or horseshoe, as is shown in FIGS. 16 and 17, to facilitate automation of the system and to minimize the footprint of the various stations and auxiliary equipment. When arranged circularly, a rotatable carriage 106 may be placed in the middle of the circle of stations for automated transfer of the pallet 34 from one station to the next. The carriage 106 comprises a plurality of arms 108 and a pallet 34 may be mounted and locked onto each arm 108. The pallets 34, when attached to the arms 108 of the carriage 106, are capable of independent up and down movement for dipping into the various tanks of the system. In this way, each pallet may be dipped into each tank independently for different amounts of time. Each arm 108 is equipped with a manual or automated raising and lowering mechanism for dipping the pallet 34 into the tanks. In the illustrated embodiment, the carriage 106 is shown with a pallet 34 attached to the arm 108 that is associated with the grafting station 49. The pallet 34 is shown being dipped into the grafting reactors 50.

In use, each of the stations are filled with their appropriate solutions. The solutions may be, for example, any of those described in Applicant's U.S. Pat. No. 6,808,738 or WO 09/015,476, the disclosures of which are incorporated by reference herein in their entireties. Suitable photoinitiators for use in the photoinitiator solution of the present invention comprise but are not limited to peresters, α-hydroxyketones, benzil ketals, benzoins and their derivatives and mixtures thereof. Specifically, suitable photoinitiators may be selected from 2,2-dimethoxy-2-phenyl-acetophenone (DPA), p-benzoyl tert-butylperbenzoate (BPB), benzophenone (BP) and mixtures thereof. One skilled in art would readily understand the type of photoinitiator that can be used in the method of the invention.

The polymerizable solution of the present invention can contain any polymerizable components that can be photografted onto the surface of a medical device. In an aspect, the polymerizable components are monomers. Suitable monomers for use in the polymerizable solution of the present invention comprise but are not limited to monomers sensitive to the presence of free radicals, that is, monomers capable of free radical polymerization such as acrylic acid, methacrylic acid, 2-carboxyethyl acrylate, 4-vinylbenzoic acid, itaconic acid, and mixtures thereof. The preferred monomer is a combination of acrylic acid and methyl acrylate.

The UV radiation for use in the grafting station 49 of the invention can be for example in the wavelength range of about 100 nm to about 400 nm. In an aspect, the wavelength range is from about 200 nm to about 400 nm, and in another aspect, from about 300 to about 400 nm.

The antimicrobial agent for use in the antimicrobial solution of the present invention is in an aspect a silver component, such as a silver salt. Silver salts suitable for use in the present invention comprise silver phosphate, silver citrate, silver lactate and mixtures thereof. However, other silver salts are suitable for use in the present invention and comprise but are not limited to silver acetate, silver benzoate, silver chloride, silver carbonate, silver iodide, silver iodate, silver nitrate, silver laurate, silver sulfadiazine, silver palmitate and mixtures thereof. The silver may be also encapsulated or associated with pharmaceutical carriers such as liposomes, micelles, microcapsules, microspheres, nanospheres and mixtures thereof. The present method and system may be conveniently used with a wide variety of silver salts leading to the slow and continued release of the silver from the surface of the device for a long and effective period of time.

Once the various tanks are filled with their appropriate solutions, the catheters are loaded onto the pallets and the pallets are attached to the arms of the carriage. Depending on the scale-up of the process that is desired, one pallet may be attached to a single arm of the carriage, or one pallet may be attached to each arm of the pallet. Therefore, up to about 10 pallets could be processed at any one time, one pallet per arm as shown in FIGS. 16 and 17, for example. It will be understood that the number of pallets can be adjusted by adjusting the number of arms on the carriage and the number of pallets being processed is considered non-limiting. Likewise, the pallets have been described as each holding 200 catheters. It will be understood that the pallets could hold fewer than 200 catheters and that, by scaling up the size of the tanks and pallets, a much larger number of catheters could be held by the pallets and processed as described herein. It will be understood that the catheters may be held in the pallets at any density, provided they do not contact one another substantially during the UV polymerization step. In an aspect, the catheters do not contact one another at all during the UV polymerization step. Different products may be held in the pallets at different densities while maintaining substantially no contact during the UV polymerization step.

Once loaded, the pallets containing the catheters proceed from station to station as has been described above. The pallets have been described above as being processed from the surface oxidation station to the photoinitiator station, the grafting station, the first wash station, the first alkaline station, the antimicrobial station, the second alkaline station, the second wash station, and the drying station in order. However, it will be understood that this order may be modified, expanded, or reduced as required by each individual process. For example, it may not be desired in all cases to coat catheters with an antimicrobial solution. In this case, the second alkaline station and the antimicrobial station may be skipped or omitted altogether. Additionally, the surface oxidation station and the first wash station are optional stations and may be skipped or omitted. It is contemplated that the system of the invention could comprise only the photoinitiator station, the grafting station, and one wash station. The grafting station may be provided on its own, with a pallet for raising and lowering the medical devices therein. The grafting station and pallet may further be provided with the photoinitiator station. Some examples of the various permutations of the modular system and method described herein are shown schematically in FIG. 1. Once the catheters have completed the entire desired coating process, they are then dried and packaged. Once sterilized the catheters are ready for sale.

The solutions described above may be replaced daily, however, the use of the supply and drain tanks facilitate the reuse of the solutions in the interest of efficiency and economy. For example, the photoinitiator solution and the antimicrobial solution may be reused for about 5 days worth of continual processing time. The ethanol wash solution may be reused for about 10 days worth of continual processing time. The other solutions may also be reused but in an aspect are replaced daily.

It will be understood that the above-described reactor, method, and system could be used for devices other than catheters. Simple modifications to the pallet construction could be made by a skilled person so as to accommodate devices other than catheters. For example, the present invention is useful with any device made of polymeric materials, such as polyurethanes, polyamides, polyesters, polyethers, polyorganosiloxanes, polysulfones, polytetrafluoroethylenes, polysiloxanes, silicone materials, poly(dimethylsiloxane)-based polymers, and the like. Such polymers are typically used clinically in a variety of medical devices comprising in-dwelling medical devices and devices in general which comprise but are not limited to cardiac valves, dressings, pins, clamps, clips, syringes and their accessories, catheters, drains, stents, implants, tubings and the like. Coating of devices such as ocular lenses and/or their delivery devices is also contemplated herein.

It will be understood that the above-described system and method may be fully automated, partially automated, or fully manual. Indeed, it is contemplated that any step referred to as "manual" may be automated instead. The pallets may be loaded, transferred from one station to the next, and unloaded manually, by machine, or by a combination thereof. The above-described method and system may further comprise a step of sterilizing the catheters before or after packaging them for sale.

EXAMPLES

Process Overview

In general, the first step in the device coating procedure involves the soaking of samples in an alcohol solution containing photoinitiators such as benzophenone (BP) and tert-butylperoxybenzoate (TBP). After a brief draining period to remove excess solution, the samples are transferred to an aqueous solution containing hydrophilic vinyl monomers such as acrylic acid (AA) and methyl acrylate (MA). Nitrogen bubbling through the monomer solution is used to purge the dissolved oxygen prior to exposure to long wavelength UV light (about 300 nm to about 365 nm). Devices with their newly-grafted hydrophilic coating are subsequently rinsed in an appropriate solvent, such as ethanol, in order to remove residual photoinitiators and monomers. The polyacrylate coating is simultaneously washed of residual monomers/polymers and activated for silver ion binding through a soaking step in an aqueous base (e.g. tris-[hydroxymethyl]aminomethane) solution. Devices with activated coatings are placed in a silver salt solution (e.g. silver acetate (AgOAc)) to bind silver ions. The silver solution may also contain silver-stabilizing agents such as pyrrolidone carboxylic acid (PCA) and/or the triarylmethane dye Brilliant Green in order to help stabilize the silver ions and to prevent discoloration of catheters. A final soaking in aqueous base solution usually completes the coating process. Catheters are then dried in air at ambient temperature over a minimum 12-hour period.

Example 1

Lubricious Silicone Foley Catheters

The general coating process described above was specifically applied to silicone Foley catheters, to render the catheters lubricious, as follows:

1. Catheters were dipped in ethanol solution of the photoinitiators BP (400 mM) and TBP (400 mM) for 6 min.
2. Catheters were dipped in aqueous monomer solution of acrylic acid (300 mM) and methyl acrylate (50 mM) and purged with $N_2$ gas for 6 min followed by irradiation with UV light for 3 min-8 min.
3. Catheters were dipped in ethanol for 5 min
4. Catheters were dipped in aqueous alkaline 50 mM Trizma solution (50±5° C.) for 10 min.
5. Catheters were washed in DI water for 10 min.
6. Catheters were dried at ambient temperature for at least 12 hours.

Example 2

Antimicrobial and Lubricious Silicone Foley Catheters

The general coating process described above was specifically applied to silicone Foley catheters, to render the catheters both antimicrobial and lubricious, as follows:

1. Catheters were dipped in ethanol solution of the photoinitiators BP (400 mM) and TBP (400 mM) for 6 min.
2. Catheters were dipped in aqueous monomer solution of acrylic acid (300 mM) and methyl acrylate (50 mM) and purged with $N_2$ gas for 6 min followed by irradiation with UV light for 3 min-8 min.
3. Catheters were dipped in ethanol for 5 min
4. Catheters were dipped in aqueous alkaline 50 mM Trizma solution (50±5° C.) for 10 min.
5. Catheters were dipped in aqueous AgOAc (10 mM), PCA (10 mM) and Brilliant Green (0.16 mM) solution for 1 min-2 min.
6. Catheters were dipped in aqueous alkaline 10 mM Trizma solution for 5 min.
7. Catheters were washed in DI water for 10 min.
8. Catheters were dried at ambient temperature for at least 12 hours.

Example 3

Antimicrobial and Lubricious Polyurethane Central Venous Catheters

The general coating process described above was specifically applied to polyurethane central venous catheters, to render the catheters both antimicrobial and lubricious, as follows:

1. Catheters were dipped in ethanol solution of the photoinitiators BP (100 mM) and TBP (100 mM) for 30 s.
2. Catheters were dipped in aqueous monomer solution of acrylic acid (200 mM) and vinyl acetamide (25 mM) and purged with $N_2$ gas for 6 min followed by irradiation with UV light for 1 min-3 min.
3. Catheters were dipped in isopropanol for 5 min.
4. Catheters were dipped in aqueous alkaline 50 mM Trizma solution (50±5° C.) for 10 min.
5. Catheters were washed in DI water for 10 min.
6. Catheters were dipped in aqueous silver lactate (10 mM), PCA (10 mM) and Crystal Violet (0.06 mM) solution for 1 min-2 min.
7. Catheters were dipped in aqueous alkaline 10 mM Trizma solution for 15 min.
8. Catheters were washed in DI water for 10 min.
9. Catheters were dried at ambient temperature for at least 12 hours.

Example 4

Antimicrobial and Lubricious Polycarbonate Spin Collars

The general coating process described above was specifically applied to polycarbonate spin collars, to render the spin collars antimicrobial and lubricious, as follows:
1. Collars were dipped in isopropanol solution of the photoinitiator BP (400 mM) for 10 min.
2. Collars were dipped in aqueous monomer solution of acrylic acid (300 mM) and methyl acrylate (50 mM) and purged with $N_2$ gas for 6 min followed by irradiation with UV light for 25 min.
3. Collars were dipped in isopropanol for 6 min.
4. Collars were dipped in aqueous alkaline 50 mM Trizma solution for 6 min.
5. Collars were dipped in aqueous AgOAc (10 mM), PCA (10 mM) and Crystal Violet (0.04 mM) solution for 10 min.
6. Collars were washed in DI water for 10 min.
7. Collars were dried at ambient temperature for at least 12 hours.

Example 5

Antimicrobial Polyoxymethylene Venous Access Port

The coating of polyoxymethylene (Delrin®) implantable ports for venous access was accomplished through an initial surface oxidation treatment followed by application of the photochemical grafting chemistry of the invention as summarized below:
1. Ports were dipped in aqueous sodium hydroxide (2 M) maintained between 85° C.-95° C. for 90 min.
2. Ports were washed in DI water for 10 min
3. Ports were dipped in tetrahydrofuran (THF) for 10 min.
4. Ports were dipped in THF solution of the photoinitiators BP (2 M) and TBP (2 M) for 6 min.
5. Catheters were dipped in aqueous monomer solution of acrylic acid (300 mM) and methyl acrylate (50 mM) and purged with $N_2$ gas for 4 min followed by irradiation with UV light for 10 min with continuous nitrogen purging.
6. Catheters were dipped in isopropanol for 6 min.
7. Catheters were dipped in aqueous alkaline 50 mM Trizma solution (50±5° C.) for 10 min.
8. Catheters were dipped in aqueous silver acetate (10 mM), PCA (10 mM) and Crystal Violet (0.30 mM) solution for 5 min.
9. Catheters were washed in DI water for 10 min.
10. Dry at ambient temperature for at least 12 hours.

The description as set forth is not intended to be exhaustive or to limit the scope of the invention. Many modifications and variations are possible in light of the above teaching without departing from the spirit and scope of the following claims. It is contemplated that the use of the present invention can involve components having different characteristics. It is intended that the scope of the present invention be defined by the claims appended hereto, giving full cognizance to equivalents in all respects.

The invention claimed is:

1. A system for grafting a coating polymer onto a surface of a device, the system comprising:
   a) a photoinitiator station comprising a photoinitiator tank for coating said device with a photoinitiator solution;
   b) a grafting station comprising:
      i) a grafting tank, for submerging said device into a polymerizable solution;
      ii) a diffuser coupled to a gas feed, disposed within said grafting tank for bubbling an oxygen-scavenging gas from said gas feed into said polymerizable solution; and
      iii) a UV light source, positioned to expose said device to UV light for activating the photoinitiator on said device; wherein said grafting is effected by submerging said device in said polymerizable solution while bubbling said gas therethrough and exposing said device to said UV light source; and
   c) a rail, for transferring said device from said photoinitiator tank to said grafting tank without first drying said device.

2. The system of claim 1, wherein the grafting tank comprises a UV light transmissible wall and the UV light source is disposed outside of said grafting tank and adjacent said wall.

3. The system of claim 2, wherein said UV light transmissible wall comprises glass.

4. The system of claim 3, wherein said glass is quartz or borosilicate glass.

5. The system of claim 4, wherein said glass is borosilicate glass.

6. The system of claim 2, comprising two opposing UV light transmissible walls.

7. The system of claim 1, wherein said rail comprises a mandrel for removably attaching said device to said rail.

8. The system of claim 7, wherein said rail and mandrel are hollow, defining a contiguous bore ending at an aperture in said mandrel, through which said oxygen-scavenging gas flows from said rail, into said mandrel, and into said polymerizable solution.

9. The system of claim 7, wherein the mandrel comprises engaging members for supporting said device.

10. The system of claim 9, wherein the engaging members are brackets.

11. The system of claim 1, wherein said rail supports a plurality of devices.

12. The system of claim 11, wherein said devices are supported on said rail such that adjacent devices do not contact one another.

13. The system of claim 12, wherein said grafting tank comprises a reactor sized to receive said rail.

14. The system of claim 13, wherein said reactor comprises an opening flanked by slanted arms, said slanted arms for guiding said rail into said opening.

15. The system of claim 13, wherein said reactor comprises a plurality of dividers for preventing adjacent devices from contacting one another.

16. The system of claim 13, comprising a plurality of reactors in tandem, each reactor sized to receive an individual rail.

17. The system of claim 1, comprising a plurality of rails arranged in rows to form a pallet.

18. The system of claim 17, wherein said pallet supports about 200 devices.

19. The system of claim 1, wherein said UV light source is a UV light assembly comprising a plurality of UV lights.

20. The system of claim 19, wherein said UV light assembly comprises a switch for independently powering each of said UV lights.

21. The system of claim 20, wherein operation of said switch is fully automated, semi-automated, or manual.

22. The system of claim 21, wherein operation of said switch is fully automated.

23. The system of claim 19, wherein said UV light assembly comprises 13 UV lights of 25 watts each.

24. The system of claim 1, wherein said diffuser is disposed inside of said grafting tank near the bottom of said tank.

25. The system of claim 24, wherein said diffuser is disposed inside of said grafting tank at the bottom of said tank.

26. The system of claim 1, wherein said gas feed is activated prior to exposing said device to said UV light source.

27. The system of claim 1, wherein gas feed is activated simultaneously with exposing said device to said UV light source.

28. The system of claim 1, wherein said gas feed is adjustable.

29. The system of claim 1, wherein said gas feed is fully automated, semi-automated, or manual.

30. The system of claim 29, wherein said gas feed is fully automated.

31. The system of claim 1, further comprising a supply tank for transferring said polymerizable solution to said grafting tank.

32. The system of claim 31, wherein said supply tank comprises a stirrer.

33. The system of claim 1, further comprising a drain tank for transferring said polymerizable solution from said grafting tank.

34. The system of claim 33, wherein said drain tank comprises a stirrer.

35. The system of claim 1, wherein the polymerizable solution is a monomer solution.

36. The system of claim 35, wherein the monomer solution is selected from the group consisting of acrylic acid, methacrylic acid, 2-carboxyethyl acrylate, 4-vinylbenzoic acid, itaconic acid, methyl acrylate, and combinations thereof.

37. The system of claim 36, wherein the monomer solution comprises acrylic acid and methyl acrylate.

38. The system of claim 1, wherein the oxygen-scavenging gas is selected from the group consisting of nitrogen, argon, helium, and combinations thereof.

39. The system of claim 38, wherein the oxygen-scavenging gas is nitrogen.

40. The system of claim 1, wherein the UV light source has a wavelength of between about 100 nm and about 400 nm.

41. The system of claim 40, wherein the UV light source has a wavelength of between about 300 nm and about 365 nm.

42. The system of claim 1, wherein said photoinitiator tank comprises a reactor sized to receive said rail.

43. The system of claim 42, wherein said reactor comprises an opening flanked by slanted arms, said slanted arms for guiding said rail into said opening.

44. The system of claim 42, wherein said reactor comprises a plurality of dividers for preventing adjacent devices from contacting one another.

45. The system of claim 42, comprising a plurality of reactors in tandem, each reactor sized to receive an individual rail.

46. The system of claim 1, wherein the photoinitiator is selected from the group consisting of peresters, α-hydroxyketones, benzil ketals, benzoins, derivatives thereof, and combinations thereof.

47. The system of claim 46, wherein the photoinitiator is selected from the group consisting of 2,2-dimethoxy-2-phenyl-acetophenone (DPA), p-benzoyl tert-butylperbenzoate (BPB), tert-butylperoxybenzoate (TBP), benzophenone (BP) and combinations thereof.

48. The system of claim 47, wherein the photoinitiator comprises benzophenone and tert-butylperoxybenzoate.

49. The system of claim 1, further comprising an antimicrobial station comprising an antimicrobial tank, said antimicrobial station for coating said device with an antimicrobial solution comprising an antimicrobial agent.

50. The system of claim 49, wherein said antimicrobial tank comprises a reactor sized to receive said rail.

51. The system of claim 50, wherein said reactor comprises an opening flanked by slanted arms, said slanted arms for guiding said rail into said opening.

52. The system of claim 50, wherein said reactor comprises a plurality of dividers for preventing adjacent devices from contacting one another.

53. The system of claim 50, comprising a plurality of reactors in tandem, each reactor sized to receive an individual rail.

54. The system of claim 49, wherein said antimicrobial agent is an antibacterial agent, an antifungal agent, or a combination thereof.

55. The system of claim 49, wherein said antimicrobial agent is selected from the group consisting of chlorhexidine, triclosan, benzalkonium chloride, ciprofloxacin, gentimicin, a silver agent, and combinations thereof.

56. The system of claim 55, wherein said silver agent is a silver salt.

57. The system of claim 56, wherein said silver salt is selected from the group consisting of silver phosphate, silver citrate, silver lactate, silver acetate, silver benzoate, silver chloride, silver carbonate, silver iodide, silver iodate, silver nitrate, silver laurate, silver sulfadiazine, silver palmitate, and combinations thereof.

58. The system of claim 57, wherein said silver salt is selected from the group consisting of silver phosphate, silver citrate, silver lactate, and combinations thereof.

59. The system of claim 49, wherein said antimicrobial agent is encapsulated and/or associated with a pharmaceutical carrier.

60. The system of claim 59, wherein said pharmaceutical carrier is selected from the group consisting of liposomes, micelles, microcapsules, microspheres, nanospheres, and combinations thereof.

61. The system of claim 49, wherein said antimicrobial solution further comprises a stabilizer.

62. The system of claim 61, wherein said stabilizer is selected from the group consisting of pyrrolidone carboxylic acid (PCA), Brilliant Green, Crystal Violet, and combinations thereof.

63. The system of claim 49, further comprising a first wash station comprising a first wash tank for rinsing said device.

64. The system of claim 63, further comprising a second wash station comprising a second wash tank for rinsing said device.

65. The system of claim 63, wherein said first wash tank comprises a wash solution selected from the group consisting of water, methanol, ethanol, isopropanol, or combinations thereof.

66. The system of claim 65, wherein said wash solution further comprises up to about 1% of a miscible organic solvent.

67. The system of claim 66, wherein said miscible organic solvent is ethyl acetate.

68. The system of claim 64, wherein said second wash tank comprises purified water.

69. The system of claim 49, further comprising a first alkaline station comprising a first alkaline tank for coating said device in a basic solution.

70. The system of claim 69, further comprising a second alkaline station comprising a second alkaline tank for coating said device in a basic solution.

71. The system of claim 69, wherein said first alkaline station further comprises a temperature control system.

72. The system of claim 71, wherein said temperature control system maintains the temperature of the basic solution within about 10° C. of the desired temperature.

73. The system of claim 72, wherein the desired temperature is between about 30° C. and about 70° C.

74. The system of claim 69, wherein said basic solution is selected from the group consisting of Trizma, sodium hydroxide, ammonia, sodium carbonate, and combinations thereof.

75. The system of claim 74, wherein said basic solution is Trizma.

76. The system of claim 1, further comprising a drying station comprising a drying chamber.

77. The system of claim 76, wherein said drying chamber comprises a drain valve for draining any residual solution that drips from said device.

78. The system of claim 76, wherein said drying station further comprises an air filtration and heating system for delivering heated air to said drying chamber.

79. The system of claim 78, wherein said heated air is at a constant temperature of between about ambient to about 70° C.

80. The system of claim 1, wherein said stations are modular and can be ordered as desired.

81. The system of claim 1, wherein said stations are disposed in tandem in a line.

82. The system of claim 1, wherein said stations are disposed in a horseshoe arrangement.

83. The system of claim 1, further comprising an arm for receiving said rail and raising and lowering said rail into each of said tanks.

84. The system of claim 83, comprising one arm per tank.

85. The system of claim 1, wherein said system is fully automated and under the control of a computer system.

86. The system of claim 1, wherein the device is selected from the group consisting of cardiac valves, dressings, pins, clamps, clips, syringes, syringe accessories, catheters, drains, stents, implants, tubings, ocular lenses, and their delivery devices.

87. The system of claim 86, wherein the device is a catheter.

88. The system of claim 1, further comprising a surface oxidation station comprising a surface oxidation tank, said surface oxidation station for pre-treating said device with a caustic aqueous solution.

89. The system of claim 88, wherein said caustic aqueous solution is selected from the group consisting of sodium hydroxide, sulfuric acid, and hydrochloric acid.

90. The system of claim 88, wherein said surface oxidation tank comprises a temperature control system.

91. The system of claim 90, wherein said temperature control system maintains the temperature of the caustic aqueous solution within about 10° C. of the desired temperature.

92. The system of claim 91, wherein the desired temperature is between about 20° C. and about 90° C.

93. The system of claim 92, wherein said surface oxidation tank comprises a removable lid.

* * * * *